United States Patent [19]

Klaveness et al.

[11] Patent Number: 5,919,753
[45] Date of Patent: Jul. 6, 1999

[54] CROSS-LINKING AGENT

[75] Inventors: Jo Klaveness, Oslo; Pål Rongved, Nesoddtangen; Per Strande, Oslo, all of Norway

[73] Assignee: Nycomed Imaging AS, Oslo, Norway

[21] Appl. No.: 08/458,611

[22] Filed: Jun. 2, 1995

Related U.S. Application Data

[63] Continuation of application No. 08/119,216, Oct. 29, 1993.

[30] Foreign Application Priority Data

Mar. 28, 1991 [GB] United Kingdom .................... 9106686
Jul. 8, 1991 [GB] United Kingdom .................... 9114678
Jan. 9, 1992 [GB] United Kingdom .................... 9200389

[51] Int. Cl.$^6$ ....................................................... C08J 9/36
[52] U.S. Cl. ...................................................... 514/2; 521/84
[58] Field of Search .................................. 521/84; 514/2

[56] References Cited

U.S. PATENT DOCUMENTS 4,251,634  2/1981  Coupek et al. ......................... 521/84

*Primary Examiner*—Cecilia J. Tsang
*Assistant Examiner*—Patrick R. Delaney
*Attorney, Agent, or Firm*—Bacon & Thomas

[57] ABSTRACT

A method of crosslinking a crosslinkable protein or carbohydrate substrate to form a crosslinked substrate in which the crosslinking groups are biodegradable. The crosslinking groups may comprise methylene diacrylate and the substrate can be galactose.

7 Claims, No Drawings

CROSS-LINKING AGENT

This application is a Continuation of application Ser. No. 08/119,216, filed Oct. 29, 1993.

This invention relates to novel crosslinking agents, more particularly to crosslinking agents capable of generating biodegradable crosslinking groups.

The use of crosslinking agents in fields such as protein and polymer chemistry is widespread and well known, e.g. for investigative or stability-enhancing purposes. The possibility of deliberately introducing biodegradable crosslinking groups has not hitherto been disclosed, but has been found by us to possess a substantial number of utilities, for example in the preparation of biodegradable polymers (e.g. as described in our copending International Patent Application No. PCT/EP91/01751), in the attachment of drugs or agricultural chemicals to polymer systems (e.g. to provide delayed release delivery systems), and in the preparation of stabilised but biodegradable and therefore rapidly eliminable ultrasound contrast agents based on microbubbles encapsulated by crosslinked liposomes or crosslinked proteins (e.g. as described in our copending British Patent Applications Nos. 9106673.8 and 9106686.0 respectively) or on microparticles of crosslinked carbohydrates, X-ray contrast agents, polypeptides and proteins (e.g. as described in our copending British Patent Application Ser. No. 9114570.6); the contents of the specifications of the aforementioned applications are herein incorporated by reference.

The crosslinking agents of the invention are characterised in that they contain, or are capable of generating during crosslinking, methylene diester or diamide groups in which the ester or amide residues are derived from a range of carbon, sulphur and phosphorus acids. Such groups are particularly rapidly degraded by common esterase enzymes but are stable in the absence of enzymes.

A small number of compounds falling within this definition have previously been described in the literature and these specific compounds per se are excluded from the scope of the invention. Thus, for example, U.S. Pat. No. 2,341,334 describes methylene dimethacrylate, ethylidene dimethacrylate and butylidene dimethacrylate as being copolymerisable with ethylenically unsaturated monomers such as vinyl acetate, methyl methacrylate or styrene; DD-A-95108 describes the preparation of benzylidene dimethacrylate and 2,2,2-trichloroethylidene dimethacrylate; U.S. Pat. No. 2,839,572 describes the preparation of a number of alkenylidene crotonates such as allylidene dicrotonate, methallylidene dicrotonate and 2-chloroallylidene dicrotonate; U.S. Pat. No. 2,568,501 describes the preparation of heptafluorobutylidene diacrylate; propylidyne trimethacrylate is described by Kimura H. in J. Osaka Univ. Dent. Sch., 20 (1980), pp. 43–49; propylidyne triacrylate is described by Cox R. J. in Polym. Prep. (Am. Chem. Soc., Div. Polym. Chem.) 29 (1988), pp. 122–123; and allylidene diacrylate and allylidene dimethacrylate are described by Arbuzova A. et al. in Zh. Obshch. Khim. 26 (1956), pp. 1275–1277. Other disclosures of the use of certain of these compounds as monomers, comonomers or crosslinking agents include Szymczak T. J. et al. in Modern Plastics (August 1974), pp. 66–68 and in West. Elec. Eng. 18 (1974), pp. 26–30; DE-A-1104700; and FR-A-2119697. Crosslinking involving the use of N,N'-methylenebis(acrylamide), and in certain cases N,N'-methylenebis(methacrylamide), is described in, for example, U.S. Pat. No. 4,743,267, U.S. Pat. No. 4,962,170, U.S. Pat. No. 5,011,864, EP-A-0383124, EP-A-0383126, CA-A-1249952, and by Capek et al., Makromol. Chem. 191 (1990), pp. 121–138 and 192 (1991), pp. 2031–2040, and Latha et al., J. Appl. Polym. Sci. 43 (1991), pp. 1159–1163.

There is no suggestion in any of the above prior art that the methylene di(carboxylic ester) or N,N'-di(carboxamide) groupings resulting from polymerisation or crosslinking might be biodegradable; indeed, the introduction of crosslinking groups of this type is generally seen as conveying enhanced rigidity and/or stability. The present invention accordingly embraces the use of these known compounds in the preparation of biodegradable crosslinked structures.

It should be noted that in the prior art crosslinking methylene di(carboxylic ester) groups are invariably present as simple carbon-attached ester groups, as a consequence of their introduction by free radical propagated reactions of e.g. alkylidene diacrylates or dimethacrylates.

Subject to the foregoing disclaimer, the novel compounds of the present invention may be regarded as crosslinking agents containing a group of formula

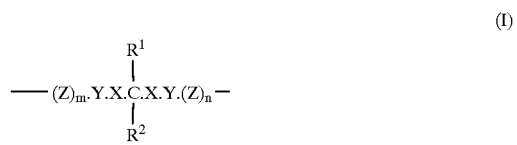

[in which each X, which may be the same or different, is selected from —O—, —S— and —NR—, where R represents a hydrogen atom or an organic group; each Y, which may be the same or different, represents carbonyl, thiocarbonyl, sulphonyl or phosphoryl (i.e. a group of formula

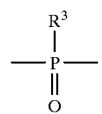

where $R^3$ is a hydrogen atom or an organic group) or a similar acid-forming group; each Z, which may be the same or different, is selected from —O—, —S— and —NR—, where R represents a hydrogen atom or an organic group; m and n, which may be the same or different, are each zero or 1; and $R^1$ and $R^2$, which may be the same or different, are each selected from hydrogen atoms, monovalent organic groups and groups of formula —X.Y.$(Z)_m$— as hereinbefore defined, or $R^1$ and $R^2$ together form a divalent organic group] or containing a group adapted to generate a group of formula (I) upon reaction with a reagent or substrate containing a species H.X.Y.$(Z)_m$— or a reactive derivative thereof.

The term "crosslinking" as used herein denotes the introduction of any desired proportion of crosslinking groups and thus generally embraces the preparation of copolymers containing linkages of formula (I).

Organic groups represented by R, $R^1$, $R^2$ and $R^3$ may, for example, each be a hydrocarbyl or heterocyclic group, for example having 1–20 carbon atoms, e.g. an aliphatic group such as an alkyl or alkenyl group (preferably having up to 10 carbon atoms), a cycloalkyl group (preferably having up to 10 carbon atoms), an araliphatic group such as an aralkyl group (preferably having up to 20 carbon atoms), an aryl group (preferably having up to 20 carbon atoms) or a heterocyclic group having up to 20 carbon atoms and one or more heteroatoms selected from O,S and N; such a hydrocarbyl or heterocyclic grouping may carry one or more substituents such as halogen atoms or groups of the formulae —$NR^4R^5$, —$CONR^4R^5$, —$OR^6$, —$SR^6$ and —$COOR^7$ (where $R^4$ and $R^5$, which may be the same or different, are hydrogen atoms, acyl groups or hydrocarbyl groups as defined for R, $R^1$, $R^2$ and $R^3$; $R^6$ is a hydrogen atom or an acyl group or a group as defined for R, $R^1$, $R^2$ and $R^3$; and $R^7$ is a hydrogen atom or a group as defined for R, $R^1$, $R^2$ and $R^3$). Where $R^1$ and $R^2$ represent a divalent grouping, this may be an alkylene, alkenylene, alkylidene or alkenylidene group (preferably having up to 10 carbon atoms) which may carry one or more substituents as defined above. In general R,$R^1$,$R^2$ and $R^3$ are preferably H or small groups such as $C_{1-4}$ alkyl groups.

Aliphatic groups R, $R^1$, $R^2$ and $R^3$ may be straight or branched, saturated or unsaturated, and include, for example, alkyl and alkenyl groups such as methyl, ethyl, isopropyl, butyl and allyl. Araliphatic groups include (monocarbocyclic aryl) alkyl groups such as benzyl. Aryl groups include mono- and bi-cyclic groups such as phenyl, tolyl and naphthyl. Heterocyclic groups include 5- and 6-membered rings preferably containing a single heteroatom, such as furyl, thienyl and pyridyl.

Possible substituents in hydrocarbyl groups R,$R^1$, $R^2$ and $R^3$ include hydroxyl, etherified hydroxyl (e.g. $C_{1-5}$ alkoxy such as methoxy), esterified hydroxyl (e.g. $C_{1-6}$ acyloxy such as acetoxy), etherified thiol, N-($C_{1-6}$ alkyl)amino, N-($C_{1-6}$ acyl)amino, N-($C_{1-6}$ acyl)-N-($C_{1-6}$ alkyl)amino, carbamoyl, N-($C_{1-6}$ alkyl) carbamoyl and halogen. Aromatic rings may carry $C_{1-6}$ alkyl groups, e.g. as in tolyl groups. Substituents may be present in combination and thus, for example, N-acyl and N-alkyl groups may carry hydroxyl or etherified or esterified hydroxyl groups.

One preferred class of compounds according to the invention may be represented by the formula

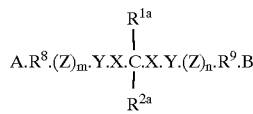

(II)

(wherein X,Y,Z, m and n are as hereinbefore defined; $R^{1a}$ and $R^{2a}$ are as defined for $R^1$ and $R^2$ except that they may represent groups —X.Y.$(Z)_m$.$R^8$.A or —X.Y.$(Z)_n$.$R^9$.B rather than groups —X.Y.$(Z)_m$—; $R^8$ and $R^9$, which may be the same or different, represent divalent organic groups optionally interrupted by one or more heteroatoms and/or carrying one or more substituents containing heteroatoms; and A and B, which may be the same or different, optionally in conjunction with the groups $R^8$ and $R^9$ to which they are attached, represent functional groupings reactive with the species to be crosslinked; with the proviso that when both A.$R^8$— and —$R^9$.B represent optionally substituted lower alk-1-enyl groups, both of X represent —O— or —NR— and both of Y represent

then at least one of m and n is 1).

A second preferred class of compounds according to the invention may be represented by the formula

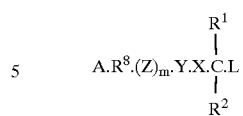

(III)

(wherein X,Y,Z, m, $R^{1a}$, $R^{2a}$, $R^8$ and A have the above-defined meanings and L is a leaving group). Such compounds may be reacted with compounds of the formula

$R^{10}$.$(Z)_n$.Y.X.H (IV)

(where X,Y,Z and n are as hereinbefore defined and $R^{10}$ represents a hydrogen atom or an organic group), or appropriate reactive derivatives thereof (e.g. alkali metal salts of compounds of formula (IV) which are acids), to generate a biodegradable linkage of formula (I).

It will be appreciated that $R^{10}$ may represent an organic group such that, for example, the compound (III) reacts to form a compound of formula (II) or a precursor therefor. Alternatively the group $R^{10}$ may represent a substrate which is to be crosslinked; in addition to the —$(Z)_n$.Y.X.H substituent or reactive derivative thereof such a substrate will also possess a functional grouping reactive with —A or —$R^8$A in formula (III).

The divalent organic groups $R^8$ and $R^9$ in the above formulae may, for example, be selected from alkylene and alkenylene groups (e.g. containing up to 30, more preferably up to 20, e.g. 1–10, carbon atoms), cycloalkylene groups (preferably having up to 10 carbon atoms), arylene groups (containing one or more aromatic rings and preferably having up to 20 carbon atoms), aralkylene groups (preferably having up to 20 carbon atoms and which may be bonded via the aryl and/or alkyl moieties—such aralkylene groups include, for example, two aryl groups joined by an alkylene chain), and heterocyclic groups (having one or more heteroatoms preferably selected from O, N and S and preferably having up to 20 carbon atoms). The groups may carry substituents, e.g. as set out above for R, $R^1$, $R^2$ and $R^3$ and/or substituents such as oxo or thio groups. The carbon chains may be interrupted by heteroatoms such as O, N, S or P, e.g. in conjunction with oxo substituents, to form linkages such as ether, ester, thioester or amide groups. The presence of disulphide linkages may also be advantageous by virtue of their inherent biodegradability.

It will be appreciated that groups $R^8$ and/or $R^9$ may be chosen so as to include one or more further groups of formula (I) and that the grouping—$R^8$.A in formula (III) may be such that it terminates in a grouping

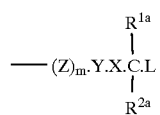

(where X, Y, Z, m, $R^{1a}$, $R^{2a}$ and L are as hereinbefore defined) capable of generating a biodegradable linkage of formula (I).

The nature of functional groups A and B will clearly depend on the nature of the species which is to be crosslinked or otherwise reacted, in particular the nature of reactive functional groupings present therein. It will be appreciated that numerous complementary pairs of interacting functional groups are known in the art, e.g. as described by Beaumert et al. in "Crosslinking techniques" (Meth.

Enzymol. 172 (1989), pp. 584–609) or in the Pierce Handbook and General Catalogue (1989), pp. 284–311.

Thus, for example, hydroxyl groups in substrates such as carbohydrates may be reacted as described in "Advances in Carbohydrate Chemistry and Biochemistry" ed. by R. Stuart Tipson and D. Horton, 33 (1976), pp. 11–109. Examples of appropriate functional groups for reacting with such substrates include halogen atoms such as chlorine or bromine, e.g. in the form of acyl halides such as alkanoyl or sulphonyl halides; sulphonyloxy groups, e.g. alkanesulphonyloxy groups such as mesyloxy groups and arenesulphonyloxy groups such as tosyloxy groups; α-halomethyl ester and keto groups; activated carboxyl groups such as symmetrical or mixed anhydrides; activated hydroxyl groups; activated alkenes, e.g. α,β-unsaturated esters, amides and ketones; conjugated diyne and enyne systems; epoxy groups; and acetal-forming aldehyde and ketone groups and derivatives thereof such as enol ethers or acetal or ketal groups.

Amino groups in substrates such as proteins may, for example, be reacted with functional groups such as activated carboxyl groups (e.g. N-hydroxysuccinimidyl derivatives, especially water solubility-enhanced sulphonated N-hydroxysuccinimidyl derivatives), imidoesters, nitroaryl halides, nitrene precursors (e.g. aryl azides such as phenylazido), carbene precursors (e.g. diazo compounds and diazirines), aldehydes, ketones, isocyanates, isothiocyanates, semicarbazides and thiosemicarbazides, epoxides, phenol esters (e.g. nitrophenol esters), acyl azides and hydrazines, haloformates, and acyl halides (e.g. alkanoyl chlorides or sulphonyl chlorides such as mesyl or tosyl chloride).

Carboxyl groups may, for example, be reacted with functional groups such as hydroxyl, mercapto, amino or diazo.

Sulfhydryl groups may, for example, be reacted with functional groups such as maleimides, sulphonated maleimides, α-halomethyl carbonyl derivatives (e.g. esters, amides or ketones), alkyl or aralkyl halides, nitrosoureas, s-triazines, aziridines and pyridyl disulphides.

Substrates containing ethylenically or acetylenically unsaturated carbon-carbon bonds (e.g. vinyl monomers such as vinyl acetate or styrene, or acrylic or methacrylic monomers such as acrylic acid, methacrylic acid, methyl acrylate, methyl methacrylate, acrylamide, methacrylamide, acrylonitrile, methacrylonitrile, hydroxyethyl methacrylate or hydroxypropyl methacrylate) may be copolymerised with compounds of formula (II) in which A and B comprise e.g. ethylenically unsaturated groups, for example under conditions appropriate for free radical polymerisation, to yield polymers containing biodegradable crosslinking groups of formula (I). It will be appreciated that in such circumstances the groups A and B may if desired form unsaturated groups in conjunction with $R^8$ and $R^9$ respectively; thus, for example, $A.R^8$— and/or —$R^9.B$ may each represent optionally substituted vinyl groups.

Leaving groups L in compounds of formula (III) include halogen atoms such as chlorine or bromine and sulphonyloxy groups such as mesyloxy or tosyloxy.

Compounds in accordance with the present invention may be prepared by any convenient method. Thus, for example, one or two equivalents of a compound of formula $$A.R^8.(Z)_m.Y.X.H \qquad (V)$$

(where X, Y, Z, m, $R^8$ and A are as hereinbefore defined, subject, if necessary and/or desired to A and any other reactive groups being protected), or a functional derivative thereof (e.g. a salt, for example an alkali metal salt such as the potassium or cesium salt of a compound (V) which is an acid), may be reacted with one equivalent of a compound of formula

(where $R^{1a}$, $R^{2a}$ and L are as hereinbefore defined) to yield compounds of formula (III) and symmetrical compounds of formula (II) respectively. Alternatively, if an unsymmetrical compound of formula (II) is required, one may, for example, react equivalent quantities of a compound of formula (V), or a functional derivative thereof, and a compound of formula

(where X, Y, Z, n, $R^{1a}$, $R^{2a}$, $R^9$, B and L are as hereinbefore defined, subject if necessary and/or desired to B and any other reactive groups being protected). Such reactions will normally be carried out in solution, for example in a polar solvent such as dimethylformamide.

Symmetrical compounds of formula (II) in which $R^{2a}$ represents a hydrogen atom, m and n are zero, each Y represents a carbonyl group and each X represents —O— may also be prepared by reacting a compound of formula $$A.R^8.CO.OH \qquad (VIII)$$

(where A and $R^8$ are as hereinbefore defined, subject, if necessary and/or desired to A and any other reactive groups being protected) with an aldehyde of formula $$R^{1a}.CHO \qquad (IX)$$

(where $R^{1a}$ is as hereinbefore defined) in the presence of an acid catalyst such as hydrochloric acid; if desired water may be removed from the reaction mixture by azeotropic distillation.

Compounds of formula (III) in which L is a halogen atom may also be prepared by reaction of a compound of formula (V) as hereinbefore defined, particularly such a compound in which Y represents a carbonyl group and X represents —O—, with an aryl thioether of formula

(where $R^{1a}$ and $R^{2a}$ are as hereinbefore defined and $R^{11}$ represents an aryl group such as phenyl), e.g. in a polar solvent such as dimethylformamide in the presence of a base such as pyridine, to yield a compound of formula

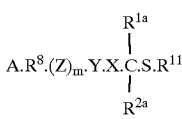

(wherein all the symbols are as hereinbefore defined) and halogenating this thioether, e.g. by reaction with sulfuryl chloride in a solvent such as dichloromethane or with bromine in a solvent such as carbon tetrachloride, to yield a compound (III) in which L is chlorine or bromine respectively.

Alternatively, compounds of formula (III) may be prepared by reaction of a compound of formula (V), as hereinbefore defined, with a chlorosulphate of formula

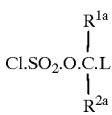

(wherein $R^{1a}$, $R^{2a}$, and L are as hereinbefore defined, L preferably being chlorine), e.g. using the method of Binderup et al. described in Synth. Comm. 14(9) (1984), pp. 857–864.

Protecting groups used in connection with A and B and any other reactive groups present may, for example, be those conventional in the art. Thus, for example, carboxyl groups may be protected using reductively cleavable ester groups such as benzyl, and hydroxyl groups may be protected using acid cleavable etherifying groups such as triphenylmethyl.

One may also prepare compounds of formulae (II) and (III) containing precursors for the desired $A.R^8$— (and/or —$R^9.B$ groups where appropriate) and subsequently convert such precursor groups to the desired reactive groupings. Thus, for example, compounds in which A and/or B represent epoxide groups may be prepared by oxidation of precursors containing appropriately positioned (e.g. terminal) ethylenically unsaturated bonds (e.g. using an oxidising agent such as metachloroperbenzoic acid), or by reacting compounds containing appropriately positioned hydroxyl groups (e.g. phenolic hydroxyl groups) with reagents such as epichlorohydrin; compounds in which $A.R^8$— and/or —$R^9.B$ represent enol ether groups may be prepared by, for example, acid-catalysed elimination from corresponding acetals or ketals. Hydroxyl group-containing precursors may also be activated by, for example, reaction with sulphonyl halides such as mesyl or tosyl chloride to generate reactive leaving groups such as mesylate or tosylate or with α,β-unsaturated alkenoyl halides such as acryloyl chloride to generate α,β-unsaturated esters.

Compounds of formula (VII) in which L represents a halogen atom may, for example, be prepared by reacting compounds of formulae

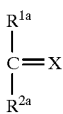

and

Hal.Y.(Z)$_n$.R$^9$.B (XIV)

(where Hal represents a halogen atom and the remaining symbols have the above-defined meanings), e.g. in the presence of a base such as pyridine.

As hereinbefore indicated, the invention embraces the use of all compounds containing a group of formula (I) or capable of reacting to generate such a group, including compounds of formula (II) subject to the aforegoing proviso regarding the definitions of X, Y, m, n, $R^8$, $R^9$, A and B, in the prepartion of substrates containing biodegradable crosslinking groups. Such uses include, for example, the previously mentioned covalent stabilisation of a range of ultrasound contrast agents, thereby enhancing the duration of attenuative activity of such agents in vivo while permitting their ready subsequent elimination from the body, and the preparation of polymers useful in the manufacture of, for example, surgical implants, soft tissue prostheses, sponges, films, wound dressings, flexible sheets, containers, plasticisers, delayed release formulations for drugs (e.g. steroids, contraceptives, antibacterials, narcotic antagonists and anti-tumour drugs) and agricultural chemicals (e.g. weed killers), and polymer particles incorporating diagnostic agents (e.g. X-ray contrast agents).

Where previously disclosed reagents such as methylene diacrylate or dimethacrylate are used in accordance with this aspect of the invention, the reaction conditions will be chosen so as to ensure biodegradability of the product, e.g. by using a non-free radical mechanism such as Michael addition of nucleophiles, for example with reactive substrate groups such as hydroxyl groups, or by effecting copolymerisation with substrates such as acrylonitrile which may polymerise by non-radical mechanisms. Free radical polymerisations should desirably be effected in such a way as to avoid formation of excessively long or tightly crosslinked carbon chains, e.g. so as to produce polymers having a molecular weight not exceeding 40,000.

The following non-limitative Examples serve to illustrate the invention.

EXAMPLE 1

Methylene dimethacrylate

A solution of potassium hydroxide (1.00M, 40.00 ml) is added to methacrylic acid (3.44 g, 40.00 mmol) at 0° C. and the solution freeze dried for 16 hours. Dry dimethylformamide (230 ml) is added and the suspension heated to 60° C. under a dry nitrogen atmosphere. Diiodomethane (1.61 ml, 20.00 mmol) is added in two portions during 10 min. and the reaction mixture left for 4 days at 60° C. The solvent is removed under reduced pressure (0.05 mm Hg), before diethyl ether (140 ml), saturated aqueous sodium hydrogen carbonate (50 ml) and water (50 ml) are added. The aqueous layer is extracted with diethyl ether (6×60 ml) and the combined ether extracts washed with water (4×50 ml), dried (MgSO$_4$), and evaporated to give 2.63 g (72%) of the title compound. $^1$H NMR (60 MHz, CDCl$_3$): δ 1.97 (2×CH$_3$, m), 5.63 (2×H-C=, m), 5.88 (CH$_2$, s), 6.18 (2×H-C=, m). IR (film, cm$^{-1}$): 2987 (w), 2962 (w), 2930 (w), 1732 (str), 1638 (w), 1454 (w), 1315 (w), 1295 (w), 1158 (w), 1100 (str), 1012 (m), 989 (m). This product may be used in accordance with the invention, for example to crosslink acrylamide polymers.

EXAMPLE 2

Methylene diacrylate

A solution of potassium hydroxide (1.00M, 40.00 ml) is added to acrylic acid (2.88 g, 40.00 mmol) at 0° C. and the solution freeze dried for 16 hours. Dry dimethylformamide (200 ml) is added and the suspension heated to 60° C. under a dry nitrogen atmosphere. Diiodomethane (1.61 ml, 20.00 mmol) is added in two portions during 10 min. and the reaction mixture left for 4 days at 60° C. The solvent is removed under reduced pressure (0.05 mm Hg), before diethyl ether (140 ml), saturated aqueous sodium hydrogen carbonate (50 ml) and water (50 ml) are added. The aqueous layer is extracted with diethyl ether (6×60 ml) and the combined ether extracts washed with water (4×50 ml), dried (MgSO$_4$), and evaporated to give 1.06 g (34%) of the title compound. $^1$H NMR (60 MHz, CDCl$_3$): δ 5.81–6.61 (2×CH$_2$=CH—, m), 5.84 (CH$_2$, s). This product may be used in accordance with the invention, for example to crosslink acrylic acid and methyl acrylate polymers.

EXAMPLE 3

Chloromethyl (2-methacryloyloxy)ethyl carbonate

Pyridine (0.89 ml, 11.00 mmol) is added dropwise to a solution of chloromethyl chloroformate (0.89 ml, 11.00 mmol) and 2-hydroxyethyl methacrylate (1.22 ml, 10.00 mmol) in dichloromethane (12 ml) at 0° C. under a dry nitrogen atmosphere. After 21 hours at 20° C. the reaction mixture is washed with hydrochloric acid (1.00M, 10 ml), saturated aqueous sodium hydrogen carbonate (10 ml) and water (10 ml). The organic phase is dried (MgSo$_4$) and the solvent evaporated under reduced pressure (10 mm Hg) to give 1.97 g (88%) of the title compound. $^1$H NMR (60 MHz, CDCl$_3$): δ 1.88 (CH$_3$, d, J=2 Hz), 4.35 (O—CH$_2$—CH$_2$—O, m), 5.47 (H—C=, m), 5.63 (CH$_2$—Cl, s), 6.00 (H—C=, m).

EXAMPLE 4

(2-Methacryloyloxy)ethyl methacryloyloxymethyl carbonate

A solution of potassium hydroxide (1.00M, 5.00 ml) is added to methacrylic acid (0.43 g, 5.00 mmol) at 0° C. and the solution freeze dried during 16 hours. Dry dimethylformamide (50 ml) is added and to the resulting suspension is added chloromethyl (2-methacryloyloxy)ethyl carboiidte (1.11 g, 5.00 mmol). 18-Crown-6 (0.066 g, 0.25 mmol) is added as a catalyst and the reaction left under a dry nitrogen atmosphere. After 24 hours at 20° C. and 6 days at 4° C. the solvent is removed under reduced pressure (0.05 mm Hg) and diethyl ether (30 ml) and water (20 ml) added. The aqueous layer is extracted with diethyl ether (3×20 ml) and the combined ether extracts washed with water (20 ml), dried (MgSO$_4$) and evaporated to give 1.26 g (93%) of the title compound. $^1$H NMR (60 MHz, CDCl$_3$): δ 1.97 (2×CH$_3$, m), 4.38 (O—CH$_2$—CH$_2$—O, m), 5.53 (2×H—C=, m), 5.77 (CH$_2$, s), 6.07 (2×H—C=, m).

EXAMPLE 5

Ethylene bis(chloromethyl carbonate)

Pyridine (0.89 ml, 11.00 mmol) is added dropwise to a solution of chloromethyl chloroformate (1.32 ml, 14.83 mmol) and ethylene glycol (0.28 ml, 5.00 mmol) in dichloromethane (10 ml) at 7° C. with good stirring under a dry N$_2$ atmosphere. After 15 min. at 7° C. and 6 hours at 20° C. the reaction mixture is transferred to a separating funnel with the aid of dichloromethane (10 ml). The reaction mixture is washed with hydrochloric acid (1.00M, 10 ml), saturated aqueous sodium hydrogen carbonate (10 ml) and water (10 ml). The organic phase is dried (MgSO$_4$) and the solvent evaporated under reduced pressure to give 1.12 g (90%) of the title product. $^1$H NMR (300 MHz, CDCl$_3$): δ 4.48 (s, O—CH$_2$CH$_2$—O), 5.75 (s, 2×Cl—CH$_2$—O). $^{13}$C NMR (75 MHz, CDCl$_3$): δ 65.8 (O—CH$_2$CH$_2$—O), 72.2 (2×Cl—CH$_2$—O), 153.0 (2×C=O).

EXAMPLE 6

Bis(2-chloromethoxycarbonyloxyethyl)ether

Pyridine (0.89 ml, 11.00 mmol) is added dropwise to a solution of chloromethyl chloroformate (1.32 ml, 14.83 mmol) and diethylene glycol (0.47 ml, 5.00 mmol) in dichloromethane (10 ml) at 7° C. with good stirring under a dry N$_2$ atmosphere. After 10 min. at 7° C. and 6 hours at 20° C. the reaction mixture is transferred to a separating funnel with the aid of dichloromethane (10 ml). The reaction mixture is washed with hydrochloric acid (1.00M, 10 ml), saturated aqueous sodium hydrogen carbonate (10 ml) and water (10 ml). The organic phase is dried (MgSO$_4$) and the solvent evaporated under reduced pressure (10 mm Hg) to give 1.26 g (86%) title product. $^1$H NMR (300 MHz, CDCl$_3$): δ 3.72 (m, 2×CH$_2$—O), 4.34 (m, 2× C$\underline{H}_2$—O—C=O), 5.71 (s, 2×Cl—CH$_2$—O). $^{13}$C NMR (75 MHz, CDCl$_3$): δ 67.6 (2×C$\underline{H}_2$—O), 68.5 (2×CH$_2$—O—C=O), 72.1 (2×Cl—CH$_2$—O), 153.2 (2×C=O).

EXAMPLE 7

1-Chloroethyl 2-methacryloyloxyethyl carbonate

Pyridine (0.89 ml, 11.00 mmol) is added dropwise to a solution of 1-chloroethyl chloroformate (1.20 ml, 11.00 mmol) and 2-hydroxyethyl methacrylate (1.22 ml, 10.00 mmol) in dichloromethane (12 ml) at 3° C. under a dry N$_2$ atmosphere. After 15 min. at 3° C. and 17 hours at 20° C. the reaction mixture is transferred to a separating funnel with the aid of dichloromethane (10 ml). The reaction mixture is washed with hydrochloric acid (1.00M, 10 ml), saturated aqueous sodium hydrogen carbonate (10 ml) and water (2×10 ml). The organic phase is dried (MgSO$_4$) and the solvent evaporated under reduced pressure to give 1.76 g (74%) of the title product. $^1$H NMR (60 MHz, CDCl$_3$): δ 1.85 (3H, d, J=6 Hz, C$\underline{H}_3$—CH), 1.96 (3H,d, J=2 Hz, CH$_3$—C=), 5.55 (1H, m, CH=), 6.10 (1H, m, CH=), 6.38 (1H, k, J=6 Hz, C$\underline{H}$—CH$_3$).

EXAMPLE 8

Chloromethyl 4-acryloyloxybutyl carbonate

Pyridine (0.89 ml, 11.00 mmol) is added dropwise to a solution of chloromethyl chloroformate (0.98 ml, 11.00 mmol) and 4-hydroxybutyl acrylate (1.38 ml, 10.00 mmol) in dichloromethane (12 ml) at 3° C. under a dry N$_2$ atmosphere. After 15 min. at 3° C. and 17 hours at 20° C. the reaction mixture is transferred to a separating funnel with the aid of dichloromethane (10 ml). The reaction mixture is washed with hydrochloric acid (1.00M, 10 ml), saturated aqueous sodium hydrogen carbonate (10 ml) and water (2×10 ml). The organic phase is dried (MgSO$_4$) and the solvent evaporated under reduced pressure to give 1.76 g (74%) of the title product. $^1$H NMR (60 MHz, CDCl$_3$): δ 1.82 (4H, m, CH$_2$—CH$_2$), 4.27 (4H, m, 2×CH$_2$—O), 5.77 (2H, s, Cl—CH$_2$—O), 5.8–6.7 (3H, m, CH=CH$_2$)

EXAMPLE 9

1-Chloroethyl 4-acryloyloxybutyl carbonate

Pyridine (0.89 ml, 11.00 mmol) is added dropwise to a solution of 1-chloroethyl chloroformate (1.20 ml, 11.00 mmol) and 4-hydroxybutyl acrylate (1.38 ml, 10.00 mmol) in dichloromethane (12 ml) at 3° C. under a dry N$_2$ atmosphere. After 15 min. at 3° C. and 17 hours at 20° C. the reaction mixture is transferred to a separating funnel with the aid of dichloromethane (10 ml). The reaction mixture is washed with hydrochloric acid (1.00M, 10 ml), saturated aqueous sodium hydrogen carbonate (10 ml) and water (2×10 ml). The organic phase is dried (MgSO$_4$) and the solvent evaporated under reduced pressure to give 2.26 g (90%) of the title product. $^1$H NMR (60 MHz, CDCl$_3$): δ

1.80 (4H, m, $CH_2$—$CH_2$), 1.86 (3H, d, J=5 Hz, $CH_3$), 4.24 (4H, m, 2×$CH_2$—O), 5.7–6.6 (4H, m, CH=$CH_2$ and CH).

EXAMPLE 10
1-Methacryloyloxyethyl 2-methacryloyloxyethyl carbonate

1-Chloroethyl 2-methacryloyloxyethyl carbonate (1.183 g, 5.00 mmol) prepared as described in Example 7 is added to a suspension of freeze dried potassium methacrylate (0.683 g, 5.50 mmol) and 18-crown-6 (0.066 g, 0.25 mmol) in dimethylformamide (50 ml) under a dry $N_2$ atmosphere. After 5 days at 20° C. the solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried ($MgSO_4$) and the solvent removed under reduced pressure to give 1.10 g (77%) of the title product. $^1H$ NMR (60 MHz, $CDCl_3$): δ 1.63 (3H, d, J=5 Hz, $\underline{CH_3}$—CH), 1.98 (6H, s, 2×$CH_3$), 4.42 (4H, s, O—$CH_2$—$CH_2$—O), 5.62 (2H, m, CH=), 6.15 (2H, m, CH=), 6.84 (1H, k, J=5 Hz, $\underline{CH}$—$CH_3$).

EXAMPLE 11
Acryloyloxymethyl 4-acryloyloxybutyl carbonate

Chloromethyl 4-acryloyloxybutyl carbonate (1.183 g, 5.00 mmol) prepared as described in Example 8 is added to a suspension of freeze dried potassium acrylate (0.606 g, 5.50 mmol) and 18-crown-6 (0.066 g, 0.25 mmol) in dimethylformamide (50 ml) under a dry $N_2$ atmosphere. After 5 days at 20° C. the solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried ($MgSO_4$) and the solvent removed under reduced pressure to give 1.24 g (91%) of the title product. $^1H$ NMR (60 MHz, $CDCl_3$): δ 1.82 (4H, m, $CH_2$—$CH_2$), 4.23 (4H, m, 2×$CH_2$—O), 5.88 (2H, s, O—$CH_2$—O), 5.7–6.8 (6H, 2×CH=$CH_2$).

EXAMPLE 12
1-Acryloyloxyethyl 4-acryloyloxybutyl carbonate

1-Chloroethyl 4-acryloyloxybutyl carbonate (1.253 g, 5.00 mmol) prepared as described in Example 9 is added to a suspension of freeze dried potassium acrylate (0.606 g, 5.50 mmol) and 18-crown-6 (0.066 g, 0.25 mmol) in dimethylformamide (50 ml) under a dry $N_2$ atmosphere. After 5 days at 20° C. the solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried ($MgSO_4$) and the solvent removed under reduced pressure to give 1.28 g (89%) of the title product. $^1H$ NMR (60 MHz, $CDCl_3$): δ 1.58 (3H, d, J=5 Hz, $\underline{CH_3}$—CH), 1.80 (4H, m, $CH_2$—$CH_2$), 4.24 (4H, m, 2×$CH_2$—O), 5.7–6.7 (6H, m, 2×CH=$CH_2$), 6.87 (1H, k, J=5 Hz, $\underline{CH}$—$CH_3$).

EXAMPLE 13
Methylene bis(p-vinylbenzoate)

Diiodomethane (0.20 ml, 2.50 mmol) is added to a solution of freeze dried potassium p-vinylbenzoate (0.931 g, 5.00 mmol), 18-crown-6 (0.040 g, 0.25 mmol) and hydroquinone (0.011 g, 0.10 mmol) in dimethylformamide (35 ml) under a dry $N_2$ atmosphere and the reaction mixture left for 2.5 days at 60° C. The solvent is removed under reduced pressure and the residue dissolved by adding diethyl ether (20 ml), saturated aqueous sodium hydrogen carbonate (5 ml) and water (10 ml). After separating the phases the aqueous layer is extracted with diethyl ether (6×10 ml) and the combined organic phase washed with water (5×10 ml). The organic phase is dried ($MgSO_4$) and the solvent removed under reduced pressure to give 0.64 g (83%) of the title product. $^1H$ NMR (300 MHz, $CDCl_3$): δ 5.39 (2H, d, J=10 Hz, 2×CH=), 5.86 (2H, d, J=17.6 Hz, 2×CH=), 6.24 (2H, s, O—CH2—O), 6.73 (2H, dd, J=11.0, 17.6, 2×CH=), 7.45 (4H, 2×d, J=6.8 Hz, Ar), 8.04 (2H, d, J=6.6 Hz, Ar), 8.05 (2H, d, J=6.6 Hz, Ar). $^{13}C$ NMR (75 MHz, $CDCl_3$): δ 79.8 (O—$CH_2$—O), 116.8 (2×CH=), 126.0, 130.2 ($C_2,C_2'$, $C_3$, $C_3'$), 127.8, 142.5 ($C_1,C_1',C_4,C_4'$), 135.7 (2×CH=), 164.9 (2×C=O).

EXAMPLE 14
Methylene bis(p-bromobenzoate)

Diiodomethane (0.60 ml, 7.50 mmol) is added to a solution of freeze dried potassium p-bromobenzoate (3.587 g, 15.00 mmol) and 18-crown-6 (0.198 g, 0.75 mmol) in dimethylformamide (100 ml) under a dry $N_2$ atmosphere and the reaction mixture left for 4 days at 60° C. The solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried ($MgSO_4$) and the solvent removed under reduced pressure to give 2.62 g (84%) of the title product. $^1H$ NMR (60 MHz, $CDCl_3$): δ 6.29 (2H, s, O—$CH_2$—O), 7.63 (4H, d, J=9 Hz, Ar), 8.00 (4H, d, J=9 Hz, Ar).

EXAMPLE 15
Methylene bis (p-hydroxybenzoate)

Diiodomethane (0.40 ml, 5.00 mmol) is added to a solution of freeze dried potassium p-hydroxybenzoate (1.762 g, 10.00 mmol) in dimethylformamide (60 ml) under a dry $N_2$ atmosphere and the reaction mixture left for 4 days at 60° C. The solvent is removed under reduced pressure and the residue dissolved by adding dichloromethane (60 ml) and water (30 ml). After separating the phases the aqueous layer is extracted with dichloromethane (3×30 ml) and the combined organic phase washed with brine (50 ml). The organic phase is dried ($MgSO_4$) and the solvent removed under reduced pressure to give 0.94 g (65%) of the title product. $^1H$ NMR (60 MHz, $CDCl_3/CD_3OD$ 1:2): δ 4.92 (2H, s, 2×OH), 6.18 (2H, s, O—$CH_2$—O), 6.88 (4H, d, J=9 Hz, Ar), 7.96 (4H, d, J=9 Hz, Ar).

EXAMPLE 16
Methylene bis[p-(hydroxymethylethynyl)benzoate]

Bis (triphenylphosphine)palladium dichloride (17.0 mg, 0.02 mmol) and cuprous iodide (2.0 mg, 0.01 mmol) are added to a suspension of methylene bis (p-bromobenzoate) (0.500 g, 1.21 mmol) prepared as described in Example 14 and propargyl alcohol (0.16 ml, 2.66 mmol) in triethylamine (10 ml) with good stirring, at 20° C., under a dry $N_2$ atmosphere. After 10 days at 20° C., the triethylamine is removed under reduced pressure, water (20 ml) is added and the mixture is extracted with dichloromethane (3×15 ml). The dichloromethane phases are washed with hydrochloric acid (0.5M, 10 ml), dried ($MgSO_4$) and the dichloromethane removed under reduced pressure to give 0.37 g (85%) of the crude product. $^1H$ NMR (60 MHz, $CDCl_3$): δ 3.67 (2H, s, OH), 4.47 (4H, s, CH$_2$—O), 6.18 (2H, s, O—CH$_2$—O), 7.2–7.5 (4H, Ar), 7.8–8.0 (4H, Ar).

EXAMPLE 17
Adipic acid bis (1-chloroethyl ester)

Anhydrous zinc chloride (10.0 mg, 0.07 mmol) is added to adipoyl chloride (2.92 ml, 20.00 mmol) at 20° C., under a dry, N$_2$ atmosphere. Acetaldehyde (2.26 g, 40.00 mmol) is added dropwise to the reaction mixture at −5° C. The reaction temperature is kept between −5° C. and 0° C. and dichloromethane (20 ml) is added. The zinc chloride catalyst is removed by passing the reaction mixture through a chromatography column containing aluminium oxide (Fluka 06290, type 5016 A basic, 20 g) at 5° C. using dichloromethane as the solvent. The solvent is removed under reduced pressure to give 3.64 g (67%) of the crude product. $^1$H NMR (60 MHz, CDCl$_3$): δ 1.5–1.9 (4H, m, CH$_2$—CH$_2$), 1.77 (6H, d, J=6 Hz, 2×CH$_3$), 2.1–2.5 (4H, m, 2×CH$_2$—O), 6.49 (2H, k, J=6 Hz, 2×Cl—CH—O).

EXAMPLE 18
Methylene bis [p-(2,3-epoxy-1-propyloxy)benzoate]

Potassium tert.butoxide (1.347 g, 12.00 mmol) is added to a solution of methylene di(p-hydroxybenzoate) (1.728 g, 6.00 mmol) prepared as described in Example 15 in DMF (75 ml), under a dry N$_2$ atmosphere. Epichlorohydrin (2.22 g, 24.00 mmol) is added and after 24 hours at 20° C. the solvent is removed under reduced pressure. The residue is dissolved by adding dichloromethane (75 ml) and water (30 ml) and adjusting the pH to neutral using hydrochloric acid (1M). After separating the phases the dichloromethane layer is washed with water (3×30 ml). The organic phase is dried (MgSO$_4$) and the solvent removed under reduced pressure to give 1.22 g (51%) product as a colourless oil. $^1$H NMR (60 MHz, CDCl$_3$): δ 2.8 (4H, m, 2×epoxy—CH$_2$), 3.3 (2H, m, 2×epoxy—CH), 4.05 (2H, dd, J=22, 11 Hz, 2×O—C$\underline{H}$—H), 4.12 (2H, dd, J=22, 11 Hz, 2×O—C$\underline{H}$—H), 6.14 (2H, s, O—CH$_2$—O), 6.9 (4H, m, 2×Ar), 7.9 (4H, m, 2×Ar).

EXAMPLE 19
Methylene bis(3,3-dimethoxypropionate)

Cesium 3,3-dimethoxypropionate (19.95 g, 75 mmol) is added to dry DMF (1000 ml). Diiodomethane (10.04 g, 37.5 mmol) is added to the suspension and the reaction mixture is stirred for 2 days at 60° C. under a dry N$_2$ atmosphere. DMF is removed under reduced pressure (0.01 mmHg). Diethyl ether (500 ml) is added to the residue, which is then washed with saturated aqueous sodium hydrogen carbonate (250 ml). The aqueous layer is extracted with diethyl ether (5×75 ml). The combined ether extracts are washed with water (2×100 ml), dried (MgSO$_4$) and evaporated to give 7.1 g (72%) product. $^1$H NMR (300 MHz, CDCl$_3$): δ 2.61 (CH$_2$, d), 3.26 (CH$_3$, s), 4.76 (CH,t), 5.70 (CH$_2$, s). $^{13}$C NMR (300 MHz, CDCl$_3$): δ 38.52 (CH$_2$), 53.37 (CH$_3$O), 79.02 (OCH$_2$O), 168.32 (C=O).

EXAMPLE 20
Methylene bis(3-methoxypropenoate)

Methylene bis(3,3-dimethoxypropionate) (14.01 g, 50 mmol) prepared as described in Example 19 and a catalytic amount of p-toluene sulfonic acid is added to toluene (250 ml). The methanol is removed by warming the reaction under an N$_2$ atmosphere. When the reaction is complete the toluene is distilled off under reduced pressure. Diethyl ether (250 ml) is added and the mixture is washed with saturated aqueous sodium hydrogen carbonate (5×50 ml) and water (3×50 ml). The organic layer is dried (MgSO$_4$) before evaporation to give 8.52 g (79%) product. $^1$H NMR (300 MHz, CDCl$_3$): δ 3.65 (2×CH$_3$, s), 5.2 (2×CH, d), 5.8 (O—CH$_2$—O), 7.65 (2×CH$_2$, d).

EXAMPLE 21
Methylene bis(10-undecenoate)

10-Undecylenic acid (12.75 g, 75 mmol) is dissolved in 100 ml water. Cesium carbonate (13.04 g, 40 mmol) is added to the mixture. The water is removed under reduced pressure and the salt dried for 2 hours in vacuo. The cesium salt is mixed with 150 ml DMF and diiodomethane is added to the solution. The reaction is stirred for 3 days at 60° C. under an N$_2$ atmosphere. DMF is then removed under reduced pressure. The residue is purified through silica gel with hexane/ethyl acetate (8:2) as eluant. The solvent is evaporated to give 7.18 g (54%) product. $^1$H NMR (300 MHz, CDCl$_3$): δ 1.2–1.4 (10×CH$_2$, m), 1.6 (2×CH$_2$, m), 2.0 (2×CH$_2$, m), 2.19 (2×CH$_2$, t), 4.9 (2×H$_2$ C=, m), 5.88 (O—CH$_2$—O, s), 5.9 (2×HC=, m). $^{13}$C NMR (300 MHz, CDCl$_3$): δ 24.92–33.98 (8×CH$_2$), 79.04 (O—CH$_2$—O), 14.18 (=CH$_2$), 139.11 (=CH), 172.48 (C=O).

EXAMPLE 22
Methylene bis(10-epoxyundecanoate)

Methylene bis(10-undecenoate) (8.8 g, 25 mmol) prepared as described in Example 21 is added under an N$_2$ atmosphere to methylene chloride and cooled to 0° C. Metachloroperbenzoic acid 55% (15.75 g, 50 mmol) is added to methylene chloride (150 ml) and the organic layer is separated and dried (MgSO$_4$). The metachloroperbenzoic acid is then added dropwise to the diester. After completed addition the temperature is increased to 25° C. After 5 hours the reaction is complete. The mixture is washed with saturated aqueous sodium sulphite (75 ml) and saturated aqueous sodium hydrogen carbonate (2×75 ml). The organic layer is purified on neutral aluminium oxide. The solvent is removed under reduced pressure to yield 8.45 g (82%) product. $^1$H NMR (300 MHz, CDCl$_3$): δ 1.2–1.7(14×CH$_2$, m), 2.35(2×CH$_2$CO,t), 2.45 (2×CH,q), 2.75 (2×CH,q), 2.90 (2×CH,m), 5.75 (O—CH$_2$—O). $^{13}$C NMR (300 MHz, CDCl$_3$): δ 24.58 (CH$_2$), 25.99 (CH$_2$), 28.94 (CH$_2$), 29.09 (CH$_2$), 29.32 (2×CH$_2$), 32.45 (CH$_2$), 33.92 (CH$_2$), 47.06 (CH$_2$—O), 52.36 (CH—O), 79.06 (O—CH$_2$—O), 172.2 (C=O).

EXAMPLE 23
Methylene bis(hydroxyacetate)

(a) Methylene bis(benzyloxyacetate)

Benzyloxyacetic acid (49.8 g, 300 mmol) is dissolved in a 500 ml mixture of water and MeOH (60:40), and cesium carbonate (48.9 g, 150 mmol) is added to the solution. The solvent is evaporated under reduced pressure and residual water is removed azeotropically with benzene. The salt is dissolved in 1500 ml DMF and diiodomethane (40.2 g, 150 mmol) is added to the solution. The reaction mixture is stirred for 3 days at 60° C. under an N$_2$ atmosphere. The DMF is removed under reduced pressure and the residue is dissolved in ether (250 ml) and washed with saturated aqueous sodium hydrogen carbonate (250 ml) and water (3×75 ml) before drying (MgSO$_4$). The solvent is evaporated and the residue is purified through silica gel with hexane/ethyl acetate (7:3) as eluant to give 23.6 g (46%) product. $^1$H NMR (300 MHz, CDCl$_3$): δ 4.1 (2×CH$_2$, s), 4.6 (2×CH$_2$, s), 5.9 (O—CH$_2$—O, s), 7.35 (2×C$_6$ H$_5$, m).

(b) Methylene bis(hydroxyacetate)

Methylene bis(benzyloxyacetate) (0.52 g, 1.5 mmol) and Pd/C (100 mg, 10%) are added to dry ethanol (100 ml). Hydrogen (1 atm) is introduced and the reaction is complete after 16 hours at room temperature, whereupon the reaction mixture is filtered and the solvent is evaporated under reduced pressure (0.01 mmHg) to yield 0.23 g (95%) product. $^1$H NMR (200 MHz, MeOH): δ 4.2 (CH$_2$, s), 4.9 (OH), 5.9 (OCH$_2$O, s). The product may be used to form polyesters with di- or poly-acids and to form polyurethanes with isocyanates.

EXAMPLE 24
Methylene bis(16-hydroxyhexadecanoate)
(a) 16-Triphenylmethoxyhexadecanoic acid A solution of 16-hydroxyhexadecanoic acid (1.36 g, 5.00 mmol), triphenylmethyl chloride (1.53 g, 5.50 mmol), triethylamine (1.25 ml) and 4-dimethylaminopyridine (10.03 g, 0.25 mmol) is stirred overnight in dry dimethylformamide at ambient temperature under nitrogen. After 16 hours stirring, the brown cloudy solution is poured into ice-water and extracted with dichloromethane (5×50 ml). The organic phases are washed with saturated ammonium chloride solution (2×100 ml), water (2×100 ml) and dried over MgSO$_4$. The solvent is removed under reduced pressure and the product purified by flash chromatography on a silica column with dichloromethane/methanol (20:1) as eluant to yield the title compound as a yellow oil (0.41 g). $^{13}$C NMR (75 MHz, CDCl$_3$): δ 24.9, 25.7, 26.3, 29.2, 29.5, 29.6, 29.7, 30.0, 32.8, 34.1, 62.9, 63.7, 86.2, 144.5, 177.2. MS (CI): 515 (M+H)
(b) 16-Triphenylmethoxyhexadecanoic acid cesium salt Aqueous cesium carbonate (1M, 0.16 ml) is added dropwise to a solution of 16-triphenylmethoxyhexa-decanoic acid (0.16 g, 0.31 mmol) in tetrahydrofuran (10 ml) until the pH reaches approximately 8, whereupon the solvent is removed under reduced pressure and the residue dried under vacuum for 2 hours. The oily semicrystalline residue is dispersed in dry dimethylformamide (10 ml) and evaporated to dryness in vacuo. The crystalline product is used without further characterization.
(c) Methylene bis(16-triphenylmethoxyhexadecanoate)

Diiodomethane (0.04 g, 0.16 mmol) is added to a suspension of 16-triphenylmethoxyhexadecanoic acid cesium salt (0.31 mmol) in dry dimethylformamide (10 ml). The reaction mixture is heated at 60° C. for 2 days under nitrogen. The solvent is removed in vacuo, and the product purified by flash chromatography on a 2×5 cm silica column with chloroform as eluant to yield the title compound as a brown oil (0.10 g). $^{13}$C NMR (75 MHz, CDCl$_3$): δ 24.6, 26.3, 29.0, 29.2, 29.4, 29.5, 29.6, 29.7, 30.0, 34.0, 63.7, 79.0, 86.2, 126.7, 127.2, 127.6, 127.9, 128.7, 144.5, 172.5.
(d) Methylene bis(16-hydroxyhexadecanoate)

Methylene bis(16-triphenylmethoxyhexadecanoate) (0.07 g, 0.07 mmol) is dissolved in glacial acetic acid (8 ml) and heated at 55° C. The reaction is monitored by TLC. After 10 hours the reaction mixture is poured onto ice, and the crude product is filtered, washed with aqueous sodium bicarbonate and water, and dried under reduced pressure. The product is purified by flash chromatography on a silica column with chloroform/methanol (20:1) as eluant to yield the title compound as a white solid. $^1$H-NMR (300 MHz, CDCl$_3$): δ 1.2–1.4(m, 44H), 1.5–1.6(m, 8H), 2.35(t, 4H), 3.64(t, 4H), 5.75(s, 2H).

EXAMPLE 25
Methylene bis(hydrogen azelate)
(a) Benzyl hydrogen azelate

Toluene-4-sulfonic acid monohydrate (0.71 g, 3.72 mmol) is added to a suspension of azelaic acid (25.0 g, 132.82 mmol) in benzene (550 ml). The mixture is heated to 80° C., whereafter benzyl alcohol (14.36 g, 132.82 mmol) in benzene (50 ml) is added dropwise to the resulting solution. The reaction mixture is refluxed overnight and water is removed azeotropically with a Dean Stark trap. The reaction mixture is allowed to cool, the white precipitate which forms is removed by filtration and the filtrate is concentrated to a brownish oil under reduced pressure. The crude product (33.97 g) is dissolved in dichloromethane (50 ml) and purified by flash chromatography, on a 5.5×15 cm silica column with dichloromethane/methanol (20:1) as eluant. The product, a yellow oil, is dried under vacuum. The oil crystallizes after a few hours at room temperature. Yield: 12.8 g (35%). $^{13}$C NMR (75 MHz, CDCl$_3$): δ 24.5, 24.8, 28.8, 34.0, 34.2, 66.1, 128.2, 128.5, 136.1, 173.6, 180.0.
(b) Cesium benzyl azelate Aqueous cesium carbonate (1M, 6.3 ml) is added dropwise to a solution of benzyl hydrogen azelate (3.00 g, 10.77 mmol) in 75 ml water/methanol (1:15) until the pH reaches approximately 7, whereupon the solvent is removed under reduced pressure and the residue dried under vacuum overnight. The oily, yellowish semicrystalline residue is dispersed in dry dimethylformamide (50 ml) and evaporated to dryness in vacuo. This procedure is repeated twice, yielding an off-white crystalline product. The product is used without further characterization.
(c) Methylene bis(benzyl azelate)

Diiodomethane (1.44 g, 5.37 mmol) is added to a suspension of cesium benzyl azelate (4.41 g, 10.77 mmol) in dry dimethylformamide (75 ml) under nitrogen. The reaction mixture is heated at 60° C. for 2 days, whereafter the solvent is removed under reduced pressure and the residue is transferred to an extraction funnel with ethyl acetate (150 ml) and water (75 ml). The organic phase is extracted with water (3×50 ml), dried over MgSO$_4$ and concentrated to a yellow oil in vacuo. Yield: 2.86 g (95.6%). $^{13}$C NMR (75 MHz, CDCl$_3$): δ 24.4, 24.8, 28.7, 28.8, 28.9, 33.8, 34.2, 66.0, 79.0, 128.1, 128.5, 136.1, 172.3, 173.5.
(d) Methylene bis(hydrogen azelate) Methylene bis(benzyl azelate) (10 g, 17.58 mmol) is dissolved in glacial acetic acid (250 ml). 10% Pd/C (2.0 g) is added, and hydrogen gas is bubbled through the solution for 2 hours. The reaction is monitored by TLC. The catalyst is removed by filtration and the solvent is removed under reduced pressure. The crude product is dissolved in diethyl ether and petroleum ether is added. An oil precipitates, which crystallizes after 1 hour. The mixture is left in a refrigerator overnight before the crystals are collected by filtration and dried under vacuum, to yield the title compound. Yield: 5.33 g (78%). $^{13}$C NMR (75 MHz, CDCl$_3$): δ 24.5, 24.6, 28.7, 28.8, 33.9, 79.1, 172.5, 180.0. mp: 57–60° C.

EXAMPLE 26
Methylene bis(hydrogen tetracosanedioate)
(a) Benzyl hydrogen tetracosanedioate Toluene-4-sulfonic acid monohydrate (0.05 g, 0.28 mmol) is added to a suspension of tetracosanedioic acid (5.0 g, 80%, 10.03 mmol) in benzene (180 ml). The mixture is heated to 80° C., whereafter benzyl alcohol (1.08 g, 10.03 mmol) in benzene (10 ml) is added dropwise to the resulting solution. The reaction mixture is refluxed for 20 hours and water is removed azeotropically with a Dean Stark trap. The solvent is removed under reduced pressure and the residue washed with petroleum ether. The product is dissolved in refluxing diethyl ether and purified by flash chromatography on a silica column with methylene chloride/methanol (20:1) as eluant to yield the title compound as a white crystalline solid. $^{13}$C NMR (75 MHz, CDCl$_3$): δ 24.0, 28.5, 29.7, 30.9, 34.4, 66.2, 128.2, 128.5, 136.0, 174.1, 176.9.
(b) Methylene bis(hydrogen tetracosanedioate)

The product from (a) above is reacted in similar manner to that described in Example 25 (b)–(d) to yield the title compound.

EXAMPLE 27
Methylene bis(4-pentenoate)

4-Pentenoic acid (10 g, 100 mmol), diiodomethane (13.4 g, 50 mmol) and 1,8-diazabicyclo[5.4.0]undec-7-ene (15.25 g, 100 mmol) are dissolved in acetonitrile (150 ml). The solution is refluxed under nitrogen for 3 hrs, whereafter acetonitrile is removed under reduced pressure. The residue is dissolved in water (75 ml) and extracted with diethyl ether (3×100 ml). The combined ether extracts are washed with saturated aqueous sodium carbonate (50 ml), dried (MgSO$_4$) and evaporated to give 8.39 g (79%) product. $^{13}$C NMR (75 MHz, CDCl$_3$): δ 28.48 (2×CH$_2$), 33.20 (2×CH$_2$), 79.11 (O—CH$_2$—O), 115.80 (2×H$_2$C=), 136.18 (2×=CH—), 171.68 (2×C=O).

EXAMPLE 28
Methylene bis(4-epoxyyentanoate)

Metachloroperbenzoic acid (15.68 g, 55%, 50 mmol) is dissolved in methylene chloride (200 ml). Water is separated and the organic layer is dried (MgSO$_4$). The resulting metachloroperbenzoic acid solution is added dropwise to methylene bis(4-pentenoate) (4.10 g, 19 mmol) dissolved in methylene chloride (50 ml). The mixture is stirred at ambient temperature under nitrogen for 12 hrs, whereafter the reaction mixture is washed with saturated aqueous sodium bicarbonate solution (50 ml), water (50 ml), dried (MgSO$_4$) and evaporated to give 3.61 g (78%) of the title compound as a crystalline product. $^1$H NMR (300 MHz, CDCl$_3$): δ 1.70–1.85 (2×CH,m), 1.95–2.10 (2×CH,m), 2.50–2.55 (2×CH, 2×CH$_2$,m), 2.75 (2×CH,t), 3.0 (2×CH,m), 5.8 (O—CH$_2$—O, s). $^{13}$C NMR (75 MHz, CDCl$_3$): δ 27 (2×CH$_2$), 30 (2×CH$_2$), 47 (2×CH$_2$), 51 (2×CH), 79.8 (O—CH$_2$—O), 171.8 (2×C=O).

EXAMPLE 29
Methylene bis(2-butenoate)

Vinylacetic acid (4.3 g, 50 mmol) is added to an aqueous cesium carbonate solution (50 ml). The mixture is stirred for 5 min. and then evaporated, and the residue is dried under vacuum for 2 hrs. The resulting cesium salt and diiodomethane are added to dimethylformamide (200 ml) and the mixture is stirred for 24 hrs. at 50° C. under nitrogen, whereafter the dimethylformamide is removed under reduced pressure. The residue is dissolved in diethyl ether (100 ml) and washed with saturated aqueous sodium bicarbonate (25 ml) and water (25 ml). The organic layer is dried (MgSO$_4$) and evaporated to give 1.32 g (29%) product. $^1$H NMR (300 MHz, CDCl$_3$): δ 1.9 (2×CH$_2$,m), 5.8–5.9 (2×CH, m), 5.9 (OCH$_2$O,s), 7.0–7.1 (2×CH,m).

EXAMPLE 30
Methylene bis(chloroacetate)

Chloroacetic anhydride (12.75 g, 75 mmol), paraformaldehyde (2.25 g, 75 mmol) and conc. sulfuric acid (15 drops) are added to methylene chloride (15 ml). The mixture is stirred for 24 hrs. at 50° C. under nitrogen, whereafter the reaction mixture is extracted with saturated aqueous potassium carbonate until carbon dioxide emission ends. The organic layer is dried (MgSO$_4$), evaporated to dryness and the residue is distilled (80° C., 0.15 mmHg) to yield 10.2 g (57%) product. $^1$H NMR (200 MHz, CDCl$_3$): δ 4.1 (2×CH$_2$Cl,s), 5.9 (CH$_2$,s). $^{13}$C NMR (200 MHz, CDCl$_3$): δ 41.1 (CH$_2$Cl), 81.4 (O—CH$_2$—O), 166.4 (CO).

EXAMPLE 31
Methylene bis(4-oxopentanoate)

4-Oxopentanoic acid (11.6 g, 100 mmol) is dissolved in acetonitrile (70 ml), and 1,8-diazabicyclo[5.4.0]undec-7-ene (15.25 g, 100 mmol) diluted with acetonitrile (30 ml) is added. Diiodomethane (13.4 g, 50 mmol) is added in one batch, and the reaction mixture is refluxed under a nitrogen atmosphere. After 2 hours, gas chromatography indicates full consumption of diiodomethane. The solvent is removed in vacuo and the residual brown oil is transferred to a separation funnel with ethyl acetate (200 ml) and water (75 ml). The organic phase is washed with 1M sodium bicarbonate (25 ml) and water (3×25 ml), dried over MgSO$_4$, and the solvent is removed in vacuo to yield the title compound (10 g). $^1$H NMR: δ 2.19 (2×CH$_3$, s), 2.760–2.804 (2×CH$_2$, t), 2.600–2.645 (2×C$_2$, t), 5.735 (CH$_2$ bridge, s).

EXAMPLE 32
Methylene bis(hydrogen glutarate)

(a) Benzyl hydrogen qlutarate

A suspension of glutaric anhydride (50 g, 430 mmol) in benzyl alcohol (54 g, 500 mmol) is heated at 105° C. overnight, whereafter gas chromatography indicates full consumption of the anhydride. Purification of a 1.3 g sample by flash chromatography on a 2.5×15 cm silica column with chloroform and methanol/chloroform (1:10) as eluants yields title compound (1.1 g). $^1$H NMR: δ 1.945–1.993 (CH$_2$, m), 2.397–2.470 (2×CH$_2$, m), 5.117 (CH$_2$, s), 7.332–7.357 (C$_6$H$_5$, m). The remaining crude product is purified by short path distillation; the main fraction is collected at 150–160° C./0.04 mmHg. Yield: 90 g.

(b) Cesium benzyl glutarate

Crude benzyl hydrogen glutarate (25 g, 100 mmol) is stirred in water (100 ml) to form a slurry. An aqueous solution of 1M cesium carbonate is added until the pH reaches 7 (52 ml is consumed). The homogeneous reaction mixture is diluted with water (150 ml), and extracted with chloroform (2×50 ml) to remove nonpolar impurities from the crude starting material. Water is removed in vacuo, and the oily, grayish semicrystalline residue is slurried in dimethylformamide (200 ml), and evaporated to dryness in vacuo. This procedure is repeated twice, yielding an off-white crystalline product, which is used without further characterization.

(c) Methylene bis(benzyl qlutarate)

Cesium benzyl glutarate (100 mmol) is slurried in dimethylformamide (150 ml). Diiodomethane (13.4 g, 50 mmol) is added, and the reaction mixture is heated at 70° C. overnight under a nitrogen atmosphere. The resulting reaction mixture is a dark, brownish slurry, which is rendered homogeneous by addition of water (50 ml). The solvent is removed in vacuo, and the residue is transferred to an extraction funnel with ethyl acetate (200 ml) and water (100 ml). The organic phase is extracted with water (2×50 ml), dried over MgSO$_4$, and concentrated in vacuo to a brownish oil (15.5 g). 0.5 g of this product is purified by flash chromatograpy on a 2.5×15 cm silica column with methylene chloride and nethanol/chloroform (1:10) as eluants to yield the title compound. $^1$H NMR (300 MHz, CDCl$_3$): δ 1.94–1.99 (2×CH$_2$, q), 2.40–2.44 (4×CH$_2$, t), 5.11 (2×CH$_2$, s), 5.28 (CH$_2$ bridge, s), 7.33–7.35 (2×C$_6$H$_5$, m). The main part of the product is used without further purification.

(d) Methylene bis(hydrogen glutarate)

Crude methylene bis(benzyl glutarate) (10 g, 22 mmol) is dissolved in a mixture of acetic acid (50 ml) and tetrahydrofuran (25 ml). 10% Pd/C (1.5 g) is added, and hydrogen gas is bubbled through the solution for 3 h. The reaction is monitored by TLC. The catalyst is removed by filtration and the solvent is removed in vacuo. The crude product is dissolved in diethyl ether and hexane is added. An oil precipitates. After a few hours in a refrigerator, the oil crystallizes. The crystals are collected by filtration and dried under vacuum. Yield: 5 g (80%). $^{13}$C NMR (75 MHz, CDCl$_3$): 171.627 ppm (CO—bridge), and 179.198 ppm (CO—free acid).

EXAMPLE 33
Methylene bis(succinimidylazelate)

1-(3-Dimethylaminopropyl)-3-ethylcarbodiimide hydrochloride (1.49 g, 7.71 mmol) was added in portions to a stirred solution of methylene bis(hydrogen azelate) from Example 25 (1.00 g, 2.57 mmol) and N-hydroxysuccinimide (0.89 g, 7.71 mmol) in dry dimethylformamide at ambient temperature. After 20 hours stirring, the reaction mixture was poured into ice-water, whereupon the product precipitated as an oil. The colourless oil was dissolved in diethylether (50 ml), washed with water (3×10 ml) and dried over MgSO$_4$. The solvent was removed under reduced pressure and hexane (5 ml) was added to the oily product. After seven days storage at 4° C. the oil had crystallized to a white, waxy solid. Yield: 1.50 g (69%). m.p.: 45–47° C. $^{13}$C NMR (75 MHz, CDCl$_3$): δ 24.42, 24.46, 25.59, 28.48, 28.63, 30.85, 33.82, 79.61, 168.6, 169.30, 172.34.

EXAMPLE 34
Methylene bis(16-acryloyloxyhexadecanoate)

Triethylamine (0.29 g, 2.87 mmol) in dry toluene (2 ml) was added to a suspension of methylene bis(16-hydroxydecanoate) from Example 24 (0.20 g, 0.36 mmol) in dry toluene (5 ml). The mixture was heated to 50° C. under nitrogen and acryloylchloride (0.26 g, 2.87 mmol) in dry toluene (3 ml) was then added dropwise. After 1 hour of stirring at 55° C. the reaction mixture was cooled to room temperature, diluted with toluene (10 ml), washed with water (2×5 ml) and dried over MgSO$_4$. The solvent was evaporated under reduced pressure to give a yellow solid product. Yield: 0.2 g (92%). MS (CI): 665 (M+H). $^{13}$C NMR (75 MHz, CDCl$_3$): δ 24.62, 25.93, 28.62, 29.01, 29.24, 29.26, 29.45, 29.52, 29.58, 29.60, 29.64, 33.98, 64.72, 78.99, 128.64, 130.43, 166.33, 172.52.

EXAMPLE 35
Methylene bis(10-methyl-6,8-dioxa-5,7-dioxoundecanoate)

Methylene bis(hydrogen glutarate) (1 g, 3.6 mmol) is dissolved in 25 ml dry acetone. Triethylamine (1 ml, 7.2 mmol) is added, and the reaction mixture is cooled to 0° C. Isobutylchloroformate (0.99 ml, 7.2 mmol) is added. The cooling bath is removed after 1 hour and stirring is continued for 1 hour. The reaction mixture is filtered and the solvent is removed in vacuo. The product is characterised by NMR, and is used without further purification.

EXAMPLE 36
Methylene bis(4-fluorocarbonyl butyrate

Methylene bis(hydrogen glutarate) (1 g, 3.6 mmol) is reacted with cyanuric fluoride as described by Olah et al., Synthesis (1973) 487–488. The product is characterised by NMR and used without further purification.

EXAMPLE 37
Methylene bis(10-oxodecanoate)

a) Methylene bis(10,11-dihydroxyundekanoate)

N-Methylmorpholine-N-oxide (13.5 g, 11 mmol) and methylene bis(10-undecenoate) from Example 21 (19 g, 5 mmol) were dissolved in 400 ml of a mixture of tetrahydrofuran and water (3:1 v/v). A catalytic amount of osmium tetroxide was added, and the solution stired at ambient temperature for 20 hours. TLC indicated complete consumption of the starting material. Excess sodium hydrogen sulphite and sodium chloride were then added to the reaction mixture. The product was extracted from the resulting mixture with ethyl acetate (400 ml) and the water phase was washed with ethyl acetate (3×50 ml). The combined organic phases were dried and evaporated, and the product recrystallised from tetrahydrofuran to yield 14.5 g (68%) of the product as a white solid. $^{13}$C NMR (45 MHz) CD$_3$OD:δ 24.6–34.0 (16×CH$_2$), 66.6 (2×CH$_2$OH), 72.3 (2×CHOH) 79.2 (O—CH$_2$—O), 174.0 (2×C=O).

b) Methylene bis(10-oxodecanoate)

Methylene bis(10,11-dihydroxyundecanoate) (2.24 g, 5 mmol) was dissolved in 150 ml tetrahydrofuran. Sodium metaperiodate (2.06 g, 10 mmol) was dissolved in 150 ml water and added dropwise to the tetrahydrofuran solution. TLC indicated full consumption of the diol after 60 minutes, whereupon sodium chloride was added to the reaction mixture until the two phases separated. The water phase was extracted with diethyl ether (3×50 ml). The combined organic phases were dried with magnesium sulphate and evaporated to give the title product as an oil, 1.43 g (74%). $^{13}$C NMR (45 MHz) CDCl$_3$: δ 21.9–43.9 (16×CH$_2$), 79.1 (O—CH$_2$—O), 173.0 (2×C=O), 202.6 (2×CHO).

EXAMPLE 38
Methylene bis(sulphosuccinimidylazelate) sodium salt

Methylene bis(hydrogen azelate) (0.38 g, 1 mmol), N-hydroxysulphosuccinimide sodium salt (0.48 g, 2.2 mmol) and dicyclohexylcarbodiimide (0.45 g, 2.2 mmol) was dissolved in dimethylformamide (10 ml). The suspension was stirred overnight at room temperature under a nitrogen atmoshphere. The reaction mixture was filtered and purified by reversed phase chromatography (RP-8) with water/acetonitrile (1:1) as eluant to give the title compound.

The following Examples from the specification of the above referenced International Patent Application Number PCT/EP91/01751 illustrate the use of cross-linking agents according to the invention in the preparation of biodegradable polymers and the attachment of drugs and agricultural chemicals thereto.

EXAMPLE 39
a) Acrylamide polymer powder crosslinked with 5% methylene dimethacrylate Methylene dimethacrylate prepared as described in Example 1 (0.50 g, 2.72 mmol) dissolved in dimethylformamide (2 ml) is added to a solution of acrylamide (10.00 g, 140.70 mmol) and azobisisobutyronitrile (AIBN, 0.02 g, 0.86 mmol) in dimethylformamide and the reaction mixture heated to 60° C. under a dry nitrogen atmosphere. After approximately 50 min. the clear reaction mixture turns into a white suspension. The reaction mixture is kept at 60° C. for a total of 2 hours to complete the reaction. After cooling to 20° C. the reaction mixture is filtered, the solid washed several times with dimethylformamide and dried under vacuum to yield the title compound as a powder. The product is insoluble in water in contrast to uncrosslinked polyacrylamide prepared by the same method. IR (KBr, cm$^{-1}$): 3379 (broad, str), 3199 (str), 2932 (w), 1739 (m), 1662 (str), 1616 (str), 1451 (m), 1415 (m), 1348 (w), 1320 (w), 1102 (w), 976 (w), 610 (broad, m). On subtracting the spectrum of polyacrylamide prepared using the same procedure as above from the crosslinked polyacrylamide, the following peaks originating from the incorporated crosslinker appear: 1740 (str), 1471 (w), 1387 (w), 1152 (m), 1084 (str), 963 (str).

b) Acrylamide polymer gel crosslinked with 5% methylene dimethacrylate

AIBN (0.01 g, 0.43 mmol) is added to a solution of acrylamide (5.00 g, 70.34 mmol) and methylene dimethacrylate prepared as described in Example 1 (0.250 g, 1.36 mmol) in water/DMSO (90:10,20 ml) at 60° C. under a dry nitrogen atmosphere, with good stirring. After approximately 25 min. the reaction mixture turns into a gel and is kept at 60° C. for a total of 2 hours to complete the reaction. The resulting gel is not soluble in water whereas the corresponding acrylamide homopolymer is soluble.

c) Acrylamide polymer crosslinked with 2.6% methylene dimethacrylate

AIBN (0.01 g, 0.43 mmol) is added to a solution of acrylamide (5.00 g, 70.34 mmol) and methylene dimethacrylate prepared as described in Example 1 (0.131 g, 0.709 mmol) in water/DMSO (90:10,20 ml) at 60° C. under a dry nitrogen atmosphere, with good stirring. After approximately 25 min. the reaction mixture turns into a gel and is kept at 60° C. for a total of 2 hours to complete the reaction. The resulting gel is not soluble in water whereas the corresponding acrylamide homopolymer is soluble.

d) Acrylamide polymer crosslinked with 1.3% methylene dimethacrylate

AIBN (0.01 g, 0.43 mmol) is added to a solution of acrylamide (5.00 g, 70.34 mmol) and methylene dimethacrylate prepared as described in Example 1 (0.065 g, 0.035 mmol) in water/DMSO (90:10, 20 ml) at 60° C. under a dry nitrogen atmosphere, with good stirring. After approximately 25 min. the reaction mixture turns into a gel and is kept at 60° C. for a total of 2 hours to complete the reaction. The resulting gel is not soluble in water whereas the corresponding acrylamide homopolymer is soluble.

The degree of swelling in water of acrylamide-methylene dimethacrylate copolymer gels prepared according to this Example is inversely proportional to the degree of crosslinking as determined by the percentage of methylene dimethacrylate employed.

EXAMPLE 40

Polymer gel containing chloramphenicol, prepared by radical polymerization of a water/DMSO (90:10) solution of the drug, acrylamide and methylene dimethacrylate AIBN (0.010 g, 0.061 mmol) is added to a solution of acrylamide (5.00 g, 70.34 mmol), methylene dimethacrylate prepared as described in Example 1 (0.250 g, 1.36 mmol) and chloramphenicol (0.051 g, 0.157 mmol) in water/DMSO (90:10, 20 ml) at 60° C. under a dry $N_2$ atmosphere, with good stirring. AIBN (0.010 g, 0.061 mmol) is again added after 1.5 hours After a total of 3 hours the reaction mixture is cooled to 20° C. The reaction mixture then proves to be a soft gel. The gel does not dissolve in water, even after 7 days, whereas the corresponding acrylamide homopolymer is water-soluble.

EXAMPLE 41

Emulsion copolymerisation of methylene dimethacrylate and methyl methacrylate 50 ml of a 1% wt/vol solution of sodium dodecyl sulphate in water is pre-heated to 60° C. under a nitrogen atmosphere. 0.20 g (1.09 mmol) of methylene dimethacrylate prepared as described in Example 1 and 9.80 g (0.098 mol) of methyl methacrylate monomer are added under vigorous stirring. The polymerisation is initiated with a metabisulphite/persulphate redox system comprising 1.6 mg (7.2 μmol) potassium metabisulphite and 0.08 mg (0.3 μmol) potassium persulphate. The polymerisation is permitted to proceed for 8 hours before cooling to room temperature. The resultant emulsion has a solids content of 11.1% which corresponds to a degree of conversion of 66%. The recovered polymer is not soluble in THF, a good solvent for poly(methyl methacrylate), indicating that the polymer is crosslinked.

EXAMPLE 42

Emulsion copolymerisation of methylene dimethacrylate and styrene 50 ml of a 1% wt/vol solution of sodium dodecyl sulphate in water is pre-heated to 60° C. under a nitrogen atmosphere. 0.20 g (1.09 mmol) of methylene dimethacrylate prepared as described in Example 1 and 9.80 g (0.094 mol) styrene monomer are added under vigorous stirring. The polymerisation is initiated with a metabisulphite/persulphate redox system comprising 1.6 mg (7.2 μmol) potassium metabisulphite and 0.08 mg (0.3 μmol) potassium persulphate. The polymerisation is permitted to proceed for 8 hours before cooling to room temperature. The resultant emulsion has a solids content of 11.2% which corresponds to a degree of conversion of 68%. The recovered polymer is not soluble in THF, a good solvent for polystyrene, indicating that the polymer is crosslinked.

EXAMPLE 43

Methyl acrylate polymer crosslinked with 2% methylene diacrylate

AIBN (0.005 g, 0.03 mmol) is added to a solution of methyl acrylate (3.029 g, 35.20 mmol) and methylene diacrylate prepared as described in Example 2 (0.110 g, 0.70 mmol) in dimethylformamide (10 ml) at 60° C. under a dry $N_2$ atmosphere. After approximately 50 min. the clear reaction mixture turns into a gel. The reaction mixture is kept at 60° C. for a total of 2 hours to complete the reaction. The resulting gel is insoluble in tetrahydrofuran, whereas poly methyl acrylate is soluble. This proves that the gel is crosslinked.

EXAMPLE 44

Acrylic acid polymer crosslinked with 2% methylene diacrylate

AIBN (0.005 g, 0.03 mmol) is added to a solution of acrylic acid (2.534 g, 35.20 mmol) and methylene diacrylate prepared as described in Example 2 (0.110 g, 0.70 mmol) in dimethylformamide (10 ml) at 60° C. under a dry $N_2$ atmosphere. After approximately 60 min. the clear reaction mixture turns into a gel. The reaction mixture is kept at 60° C. for a total of 2 hours to complete the reaction. The resulting gel is insoluble in dimethylformamide, whereas poly acrylic acid is soluble. This proves that the gel is crosslinked.

EXAMPLE 45

Acrylamide polymer crosslinked with 0.5% methylene diacrylate

AIBN (0.005 g, 0.03 mmol) dissolved in tetrahydrofuran (2 ml) is added to a solution of acrylamide (2.500 g, 35.17 mmol) and methylene diacrylate prepared as described in Example 2 (0.027 g, 0.18 mmol) in tetrahydrofuran (10 ml) at 60° C. under a dry $N_2$ atmosphere. After approximately 2 hours no visible change is observable in the reaction mixture. AIBN (0.005 g, 0.03 mmol) is therefore added. The polymer then starts to precipitate from the reaction mixture and after a total of 5 hours the reaction mixture is cooled and filtered. The polymer is washed several times with tetrahydrofuran and dried under reduced pressure. The resulting polymer is insoluble in water, whereas polyacrylamide is soluble. This proves that a crosslinked polymer is formed. The IR-spectrum of the polymer confirms this structure. Subtracting the IR-spectrum of polyacrylamide prepared by the same procedure as above confirms the incorporation of the crosslinker. The concentration of the crosslinker (0.5%) is, however, too low to give an accurate "subtraction spectrum".

EXAMPLE 46
Polymer gel containing testosterone, prepared by radical polymerization of a water/DMSO (90:10) solution of the drug, acrylamide and methylene diacrylate AIBN (0.010 g, 0.061 mmol) is added to a solution of acrylamide (5.00 g, 70.34 mmol), methylene diacrylate prepared as described in Example 2 (0.212 g, 1.36 mmol) and testosterone (0.050 g, 0.173 mmol) in water/DMSO (90:10, 20 ml) at 60° C. under a dry $N_2$ atmosphere, with good stirring. After 40 mins. the reaction mixture has turned into a gel. The reaction mixture is kept at 60° C. for a total of 2 hours to complete the reaction. Upon cooling to 20° C. the testosterone crystallizes in the gel. The gel does not dissolve in water, whereas the corresponding acrylamide homopolymer is water-soluble.

EXAMPLE 47
Polymer gel containing 5-fluorouracil, prepared by radical polymerization of a water/DMSO (14:1) solution of the drug, acrylamide and methylene diacrylate An aqueous solution of 5-fluorouracil (5.00 ml, 250 mg/10 ml, 0.961 mmol) is added to a solution of acrylamide (5.00 g, 70.34 mmol) and methylene diacrylate prepared as described in Example 2 (0.212 g, 1.36 mmol) in water/DMSO (90:10, 10 ml) at 60° C. under a dry $N_2$ atmosphere, with good stirring. AIBN (0.010 g, 0.061 mmol) is then added and after 35 mins. the reaction mixture is turned into a gel. The reaction mixture is kept at 60° C. for a total of 2 hours to complete the reaction. The gel does not dissolve in water, whereas the corresponding acrylamide homopolymer is water-soluble.

EXAMPLE 48
Acrylamide polymer crosslinked with 0.5% 2-methacryloyloxyethyl methacryloyloxymethyl carbonate AIBN (0.005 g, 0.03 mmol) is added to a solution of acrylamide (2.500 g, 35.20 mmol) and 2-methacryloyloxyethyl methacryloyloxymethyl carbonate prepared as described in Example 4 (0.048 g, 0.18 mmol) in tetrahydrofuran (10 ml) at 60° C. under a dry $N_2$ atmosphere. After 2 hours no visible change is observed in the reaction mixture. AIBN (0.005 g, 0.03 mmol) dissovled in tetrahydrofuran (2 ml) is therefore added. The polymer then starts to precipitate from the reaction mixture and after a total of 4 hours the reaction mixture is cooled and filtered. The polymer is washed several times with tetrahydrofuran and dried under reduced pressure. IR (KBr, $cm^{-1}$): 3350 (broad, m), 3198 (m), 2933 (w), 1659 (str.), 1617 (m), 1450 (w), 1420 (w). The polymer is soluble in water giving a viscous solution, suggesting little crosslinking.

EXAMPLE 49
2-Hydroxyethyl methacrylate polymer crosslinked with 0.5% 2-methacryloyloxyethyl methacryloyloxymethyl carbonate AIBN (0.005 g, 0.03 mmol) is added to a solution of 2-hydroxyethyl methacrylate (4.578 g, 35.20 mmol) and 2-methacryloyloxyethyl methacryloyloxymethyl carbonate prepared as described in Example 4 (0.0479 g, 0.18 mmol) in tetrahydrofuran (10 ml) at 60° C. under a dry $N_2$ atmosphere. After one hour tetrahydrofuran (10 ml) is added and the reaction mixture turns into a gel. The reaction mixture is kept at 60° C. for a total of 2 hours to complete the reaction. The resulting gel is insoluble in dichloromethane, whereas poly 2-hydroxyethyl methacrylate is soluble. This proves that the gel is crosslinked.

EXAMPLE 50
Covalent attachment of MCPA to 2-hydroxyethyl methacrylate polymer crosslinked with 0.5% 2-methacryloyloxyethyl methacryloyloxymethyl carbonate The gel described in Example 49 (2.0 g) is swelled in 20 ml dry DMSO. The gel suspension is added a solution of 2-methyl-4-chloro-phenoxy acetic acid (MCPA) (2.0 g, 10 mmol), N-ethyl-N'-(3-(N"-dimethylamino)propyl) carbodiimide and 4-pyrrolidinopyridine (160 mg, 1 mmol) in 30 ml dry DMSO, under a dry nitrogen atmosphere. The suspension is shaken for 24 hours at room temperature, and the gel is washed with DMSO and finally water and dried in vacuo to yield the product. The resulting water suspensible gel contains the highly water soluble weed killer MCPA covalently attached to the gel and provides sustained release of the agrochemical.

EXAMPLE 51
Covalent attachment of 5-acetylamino-3-(N-methylacetylamino)-2,4,6-triiodobenzoic acid (Isopaque) to 2-hydroxyethyl methacrylate polymer crosslinked with 0.5% 2-methacryloyloxyethyl methacryloyloxymethyl carbonate (a) The Isopaque amide of β-alanine-O-benzyl ester Potassium carbonate (0.69, 5 mmol) is added to a solution of H-β-alanine-O-benzyl ester (1.76 g, 5 mmol) in dry dimethylformamide (50 ml) at 0° C. After 10 minutes at ambient temperature, 5-acetylamino-3-(N-methylacetylamino)-2,4,6-triiodobenzoyl chloride (Isopaque acid chloride) (3.23 g, 5 mmol) dissolved in dry dimethylformamide (20 ml) is added dropwise to the suspension at 0° C. under a nitrogen atmosphere. The reaction mixture is heated to 50° C. After 24 hours the solvent is removed under reduced pressure and chloroform (500 ml) and water (200 ml) are added. The organic phase is washed with saturated aqueous sodium hydrogen carbonate (100 ml), 0.01M HCl (100 ml) and water (2×100 ml). After drying of the organic phase evaporation of the solvent gives 3.10 g product (79%). $^1$H NMR (300 MHz): δ 1.72–1.83 (m), 2.15–2.23 (m), 2.72–2.81 (m), 3.0–3.09 (m), 3.67–3.78 (m), 5.05–5.20 (m), 6.6–7.0 (m), 7.31–7.35 (m), 8.5–8.9 (m).

(b) Debenzylation of the Isopague amide of β-alanine-O-benzyl ester

The Isopaque amide of β-alanine-O-benzyl ester prepared in (a) above (1.578 g, 2 mmol) is dissolved in dry methanol (50 ml). Palladium on charcoal (10%, 0.4 g) is added in one portion with stirring of the reaction mixture. Hydrogen gas is bubbled into the solution for two hours, and then the reaction mixture is stirred for a further 2 hours. Filtration and evaporation of the solvent yield a yellow residue, which is purified on a weakly cationic ion exchanger to yield the product.

(c) Attachment of 5-acetylamino-3-(N-methylacetylamino)-2,4,6-triiodobenzoic acid (Isopaque) to polymer gel The carboxylic acid from (b) above is attached to the gel described in Example 49 using the method described in Example 50.

EXAMPLE 52
Polymer from ethylene di(chloromethyl carbonate) and terephthalic acid Ethylene di(chloromethyl carbonate) prepared as described in Example 5 (0.489 g, 1.98 mmol) is added to a suspension of freeze dried di-potassium terephthalate (0.480 g, 1.98 mmol) and 18-crown-6 (0.027 g, 0.10 mmol) in dimethylformamide (20 ml). After 2 days at 20° C. the reaction mixture is heated to 60° C. and kept there for 3 weeks. The solvent is removed under reduced pressure and the residue dissolved by adding dichloromethane (60 ml) and water (30 ml). After separating the phases the dichloromethane phase is washed with saturated aqueous sodium hydrogen carbonate (30 ml) and brine (30 ml). The organic phase is dried (MgSO$_4$) and the solvent removed under reduced pressure to give 0.35 g (53%) of the title product. $^1$H NMR (60 MHz, CDCl$_3$): δ 4.47 (4H, s, O—CH$_2$CH$_2$—O), 6.02 (4H, s, 2×O—CH$_2$—O), 8.12(4H, s, Ar). High temperature gel filtration chromatography (GPC) indicates that fractions of the material have a molecular weight exceeding 20,000 with respect to poly(ethylene glycol) as standard.

EXAMPLE 53

Polymer from bis (2-chloromethoxycarbonyloxyethyl) ether and di-potassium fumarate Bis(2-chloromethoxycarbonyloxyethyl) ether prepared as described in Example 6 (1.456 g, 5.00 mmol) is added to a suspension of di-potassium fumarate (0.961 g, 5.00 mmol) and 18-crown-6 (0.039 g, 0.15 mmol) in DMF (50 ml) and the reaction mixture is heated to 60° C., under a dry N$_2$ atmosphere. After 11 days at 60° C. the solvent is removed under reduced pressure. Chloroform (40 ml) is added to the residue and the organic layer washed with water (3×30 ml). The combined water washings are extracted with chloroform (3×20 ml). The combined organic phases are concentrated in vacuo to give 1.57 g (94%) of a brown oil product. $^1$H NMR (300 MHz, DMSO-d$_6$, 40° C.): δ 3.78 (4H, m, 2×CH$_2$—O), 4.38 (4H, m, 2×CH$_2$—O—C=O), 5.94 (4H, s, 2×O—CH$_2$—O), 6.98 (2H, s, CH=CH). High temperature gel filtration chromatography (GPC) indicates that fractions of the material have a molecular weight exceeding 20,000 with respect to poly(ethylene glycol) as standard.

EXAMPLE 54

Methyl methacrylate polymer crosslinked with 2% acryloyloxymethyl 4-acryloyloxybutyl carbonate AIBN (0.005 g, 0.03 mmol) is added to a solution of methyl acrylate (3.029 g, 35.20 mmol) and acryloyloxymethyl 4-acryloyloxybutyl carbonate prepared as described in Example 11 (0.192 g, 0.70 mmol) in dimethylformamide (10 ml) at 60° C. under a dry N$_2$ atmosphere. After 1 hour the clear reaction mixture turns into a gel. The reaction mixture is kept at 60° C. for a total of 2 hours to complete the reaction. The resulting gel is insoluble in tetrahydrofuran, whereas poly methyl methacrylate is soluble. This proves that the gel is crosslinked.

EXAMPLE 55

Acrylamide polymer crosslinked with 2% acryloyloxymethyl 4-acryloyloxybutyl carbonate AIBN (0.005 g, 0.03 mmol) is added to a solution of acrylamide (2.502 g. 35.20 mmol) and acryloyloxymethyl 4-acryloyloxybutyl carbonate prepared as described in Example 11 (0.202 g, 0.74 mmol) in dimethylformamide (10 ml) at 60° C. under a dry N$_2$ atmosphere. After approximately 40 min. the reaction mixture turns white and the polymer starts to precipitate. The reaction mixture is cooled and filtered after a total of 2 hours at 60° C. The polymer is washed several times with dimethylformamide and dried under reduced pressure. IR (KBr, cm$^{-1}$): 3387 (broad, m), 3195 (m), 2932 (w), 2360 (w), 1661 (str.), 1611 (m), 1451 (w), 1415 (w). The polymer product is insoluble in water, whereas polyacrylamide is soluble. This proves that the polymer is crosslinked.

EXAMPLE 56

(a) Enzyme-catalyzed hydrolysis of acrylamide polymer crosslinked with 2% acryloyloxymethyl 4-acryloyloxybutyl carbonate 432 mg samples of the polymer described in Example 55 and 50 ml 0.9% NaCl (Sterile, Hydro Pharma) are added to each of two reaction vials. To one of the vials is also added 1000 μl esterase (Sigma, E-2138, 2530 U). The pH within each vial is kept constant at 8.4 by adding 0.10M NaOH. By recording the consumption of NaOH the rates of hydrolysis are calculated. During 21 hours, hydrolysis of the polymer with esterase is found to be 8.5 times faster than the control without esterase.

(b) Enzyme-catalyzed hydrolysis of acrylamide polymer crosslinked with 2% methylene dimethacrylate compared with control polyester To one vial are added 500 mg acrylamide polymer crosslinked with 2% methylene dimethacrylate prepared according to the method of Example 39(a), 40 ml (0.16M, pH 7.4) PBS (phosphate buffer) and 800 μl esterase (Sigma, E-2138, 2024 U)

As a control 500 mg acrylamide polymer crosslinked with 2% ethylene dimethacrylate (prepared according to the method of Example 39(a) but using ethylene dimethacrylate instead of methylene dimethacrylate), 40 ml (0.16M, pH 7.4) PBS (phosphate buffer) and 800 μl esterase (Sigma, E-2138, 2024 U) are added to a second vial.

For the control polyester, pH of the buffer decreases from 7.1 to 6.9 during 200 hours, while pH in the buffer solution containing acrylamide polymer crosslinked with methylene dimethacrylate decreases from 7.1 to 6.4 during 24 hours, indicating that the acid metabolites are formed much faster for methylene dimethacrylate polymer than for the control polyester.

EXAMPLE 57

Emulsion copolymerisation of acryloyloxymethyl 4-acryloyloxybutyl carbonate and methyl methacrylate 50 ml of a 1% wt/vol solution of sodium dodecyl sulphate in water is pre-heated to 60° C. under a nitrogen atmosphere. 0.20 g (0.74 mmol) of acryloyloxymethyl 4-acryloyloxybutyl carbonate prepared as described in Example 11 and 9.80 g (0.098 mol) of methyl methacrylate monomer are added under vigorous stirring. The polymerisation is initiated with a metabisulphite/persulphate redox system comprising 1.6 mg (7.2 μmol) potassium metabisulphite and 0.08 mg (0.3 μmol) potassium persulphate. The polymerisation is permitted to proceed for 8 hours before cooling to room temperature. The resultant emulsion has a solids content of 11.2% which corresponds to a degree of conversion of 67%. The recovered polymer is not soluble in THF, a good solvent for poly(methyl methacrylate), indicating that the polymer is crosslinked.

EXAMPLE 58

Emulsion copolymerisation of acryloyloxymethyl 4-acryloyloxybutyl carbonate and styrene 50ml of a 1% wt/vol solution of sodium dodecyl sulphate in water is pre-heated to 60° C. under a nitrogen atmosphere. 0.20 g (0.74 mmol) of acryloyloxymethyl 4-acryloyloxybutyl carbonate prepared as described in Example 11 and 9.80 g (0.094 mol) of styrene monomer are added under vigorous stirring. The polymerisation is initiated with a metabisulphite/persulphate redox system comprising 1.6 mg (7.2 μmol) potassium metabisulphite and 0.08 mg (0.3 μmol) potassium persulphate. The polymerisation is permitted to proceed for 8 hours before cooling to room temperature. The resultant emulsion has a solids content of 12% which corresponds to a degree of conversion of 72%. The recovered polymer is not soluble in THF, a good solvent for polystyrene, indicating that the polymer is crosslinked.

EXAMPLE 59
Acrylamide polymer crosslinked with 2% 1-acryloyloxyethyl 4-acryloyloxybutyl carbonate AIBN (0.005 g, 0.03 mmol) is added to a solution of acrylamide (2.502 g. 35.20 mmol) and 1-acryloyloxyethyl 4-acryloyloxybutyl carbonate prepared as described in Example 12 (0.202 g, 0.70 mmol) in dimethylformamide (10 ml) at 60° C. under a dry $N_2$ atmosphere. After approximately 30 min. the polymer starts to precipitate from the reaction mixture. The reaction mixture is cooled and filtered after a total of 2 hours at 60° C. The polymer is washed several times with dimethylformamide and dried under reduced pressure. IR (KBr, $cm^{-1}$): 3390 (broad, m), 3197 (m), 2933 (w), 1661 (str.), 1611 (m), 1452 (w), 1415 (w). The polymer product is insoluble in water, whereas polyacrylamide is soluble. This provides that the polymer is crosslinked.

EXAMPLE 60
Polymer gel containing magnetic starch microspheres prepared by radical polymerization of a water/DMSO (90:10) suspension of magnetic starch microspheres acrylamide and 1-acryloyloxyethyl 4-acryloyloxybutyl carbonate An aqueous suspension of magnetic starch microspheres prepared as described in WO 85/02722 (Schröder) (0.50 ml from a solution containing 7.5 mg Fe/ml, 0.9% NaCl and 0.5% glycerol) is added to a solution of acrylamide (5.00 g, 70.34 mmol) and 1-acryloyloxyethyl 4-acryloyloxybutyl carbonate prepared as described in Example 12 (0.359 g, 1.36 mmol) in water/DMSO (90:10, 10 ml) at 60° C. under a dry $N_2$ atmosphere, with good stirring. AIBN, (0.010 g, 0.061 mmol) is then added and after approximately 40 minutes the reaction mixture has turned into a gel. The reaction mixture is kept at 60° C. for a total of 2 hours to complete the reaction. The gel does not dissolve in water, whereas the corresponding acrylamide homopolymer is water-soluble.

EXAMPLE 61
Polyester from methylene di(p-hydroxybenzoate) and adipoyl chloride Pyridine (0.560 ml, 6.94 mmol) is added dropwise to a solution of methylene di(p-hydroxybenzoate) prepared as described in Example 15 (1.00 g, 3.47 mmol) and adipoyl chloride (0.635 g, 3.47 mmol) in dry dichloromethane (30 ml) at 20° C. under a dry $N_2$ atmosphere. After 18 hours at 20° C. water (10 ml) is added to the reaction mixture and the phases are separated. The aqueous layer is extracted with dichloromethane (3×10 ml) and the combined organic phases are washed with water (3×20 ml). The volume of the organic phase is increased to 250 ml by adding more dichloromethane. The resulting organic phase is dried ($MgSO_4$) and the solvent evaporated under reduced pressure (0.1 mmHg) to give 0.93 g (67%) product. $^1$H NMR (300 MHz, $CDCl_3$): δ 1.76 (4H, m, $CH_2$—$CH_2$), 2.59 (4H, m, 2×$CH_2$—C═O), 6.20 (2H, s, O—$CH_2$—O), 7.16 (4H, Ar), 8.06 (4H, Ar). High temperature gel filtration chromatography (GPC) indicates that fractions of the material have a molecular weight exceeding 20,000 with respect to poly (ethylene glycol) as standard.

EXAMPLE 62
Polymer from 1,6-diisocyanatohexane and methylene di(p-hydroxybenzoate)

1,6-Diisocyanatohexane (0.927 g, 5.51 mmol) is added to a solution of methylene di(p-hydroxybenzoate) prepared as described in Example 15 (1.588 g, 5.51 mmol) in DMF (15 ml) under a dry $N_2$ atmosphere. The reaction mixture is heated to 100° C. for 3 days before the solvent is removed under reduced pressure at 50° C. Upon cooling to 20° C. the product turns into a rubber-like material which is practically insoluble in a 1:1 mixture of chloroform and DMSO, indicating formation of a polymer.

EXAMPLE 63
Polymer from adipic acid bis 1-chloroethyl ester and di-potassium terephthalate Potassium tert.butoxide (1.122 g, 10.00 mmol) is added to a solution of terephthalic acid (0.831 g, 5.00 mmol) in DMF (50 ml) at 20° C., under a dry $N_2$ atmosphere. Adipic acid bis 1-chloroethyl ester prepared as described in Example 17 (1.356 g, 5.00 mmol) is added to the resulting suspension and the reaction mixture heated to 60° C. After 1 hour at 60° C., 18-crown-6 (0.066 g, 0.25 mmol) is added. The solvent is removed under reduced pressure after 8 days at 60° C. and the residue dissolved by adding chloroform (60 ml), ethyl acetate (30 ml) and aqueous sodium hydroxide (1M, 50 ml). After separating the phases the aqueous phase is extracted with chloroform (3×25 ml). The combined organic layers are washed with water (2×50 ml) and dried ($MgSO_4$). The solvent is removed under reduced pressure to give 0.238 g (13%) of crude product.

EXAMPLE 64
Polymer from adipic acid bis 1-chloroethyl ester and di-potassium fumarate Potassium tert.butoxide (1.122 g, 10.00 mmol) is added to a solution of fumaric acid (0.580 g, 5.00 mmol) in DMF (50 ml) at 20° C., under a dry $N_2$ atmosphere. Adipic acid bis 1-chloroethyl ester prepared as described in Example 17 (1.356 g, 5.00 mmol) is added to the resulting suspension and the reaction mixture heated to 60° C. After 1 hour at 60° C., 18-crown-6 (0.066 g, 0.25 mmol) is added. The solvent is removed under reduced pressure after 8 days at 60° C. and the residue dissolved by adding chloroform (60 ml), ethyl acetate (30 ml) and aqueous sodium hydroxide (1M, 50 ml). After separating the phases the aqueous phase is extracted with chloroform (3×25 ml). The combined organic layers are washed with water (2×50 ml) and dried ($MgSO_4$). The solvent is removed under reduced pressure to give 0.276 g (18%) of crude product.

EXAMPLE 65
Epoxy resin based on methylene bis[p-2,3-epoxy-1-propyloxy)benzoate] and an aliphatic polyamine A sample of methylene bis[p-(2,3-epoxy-1-propyloxy) benzoate] prepared as described in Example 18 is blended with an equal weight of a commercial aliphatic polyamine curing agent. This mixture is used as an adhesive to adhere two glass plates together at room temperature. The resin is observed to have hardened and good bonding is obtained within 24 hours of mixing.

EXAMPLE 66
Aqueous polymer gel prepared by crosslinking an aqueous solution of poly(vinyl alcohol) with methylene di(3,3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.8 by adding hydrochloric acid (18% solution). To this solution, 0.10 g (0.35 mmol) of methylene di(3,3-dimethoxypropionate) prepared as described in Example 19 is added, and the solution is well mixed. After 24 hours at room temperature the viscosity of the solution is higher than initially, and after 48 hours at room temperature the solution has formed a relatively strong gel. The gel is thoroughly washed with excess water for one day and stored under water to avoid drying. The water content of this gel is measured as being 98.5% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.3 by adding hydrochloric acid (18% solution). To this solution, 0.10 g (0.35 mmol) of methylene di(3,3-dimethoxypropionate) prepared as described in Example 19 is added, and the solution is well mixed. After 6 hours the solution has formed a gel and after 48 hours syneresis is observed. The gel is thoroughly washed with excess water for one day and stored under water to avoid drying. The water content for this gel is measured as being 95.5% (by volume).

(c) 5 g of an aqueous solution of poly(vinyl alcohol) (6.25 w % in water, 7.0 mmol with respect to monomer units, average M.W. 126 000, 98% hydrolyzed) is adjusted to pH=0.8 by adding hydrochloric acid (18% solution). To this solution is added 19.6 mg (0.07 mmol) of methylene di(3,3-dimethoxypropionate) prepared as described in Example 19 in 1 ml of water, and the solution is well mixed. After 3 hours at 50° C. the solution has formed a gel. The gel is thoroughly washed with excess water for one day and stored under water to avoid drying. The water content for this gel is estimated to be 98% (by volume).

(d) 5 g of an aqueous solution of poly(vinyl alcohol) (6.25 w % in water, 7.0 mmol with respect to monomer units, average M.W. 126 000, 98% hydrolyzed) is adjusted to pH=0.8 by adding hydrochloric acid (18% solution). To this solution 0.1 g (0.35 mmol) of methylene di(3,3-dimethoxypropionate) prepared as described in Example 19 is added, and the solution is well mixed. After 3 hours at 50° C. the solution has formed a gel. The gel is thoroughly washed with excess water for one day and stored under water to avoid drying. The water content for this gel is estimated to be 95% (by volume).

(e) 5 g of an aqueous solution of poly(vinyl alcohol) (6.25 w % in water, 7.0 mmol with respect to monomer units, average M.W. 126 000, 98% hydrolyzed) is adjusted to pH=0.8 by adding hydrochloric acid (18% solution). To this solution is added 19.6 mg (0.07 mmol) of methylene di(3,3-dimethoxypropionate) prepared as described in Example 19 in 1 ml of water, and the solution is well mixed. After 40 minutes at 80° C. the solution has formed a gel. The gel is thoroughly washed with excess water for one day and stored under water to avoid drying. The water content for this gel is estimated to be 98% (by volume).

(f) 5 g of an aqueous solution of poly(vinyl alcohol) (6.25 w % in water, 7.0 mmol with respect to monomer units, average M.W. 126 000, 98% hydrolyzed) is adjusted to pH=0.8 by adding hydrochloric acid (18% solution). To this solution 0.1 g (0.35 mmol) of methylene di(3,3-dimethoxypropionate) prepared as described in Example 19 is added, and the solution is well mixed. After 40 minutes at 80° C. the solution has formed a gel. The gel is thoroughly washed with excess water for one day and stored under water to avoid drying. The water content for this gel is estimated to be 95% (by volume).

(g) 5 g of an aqueous solution of poly(vinyl alcohol) (6.25 w % in water, 7.0 mmol with respect to monomer units, average M.W. 126 000, 98hydrolyzed) is adjusted to pH=0.4 by adding hydrochloric acid (18% solution). To this solution is added 19.6 mg (0.07 mmol) of methylene di(3,3-dimethoxypropionate) prepared as described in Example 19 in 1 ml of water, and the solution is well mixed. After 40 minutes at 80° C. the solution has formed a gel. The gel is thoroughly washed with excess water for one day and stored under water to avoid drying. The water content for this gel is estimated to be 98% (by volume).

(h) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution 0.1 g (0.35 mmol) of methylene di(3,3-dimethoxypropionate) prepared as described in Example 19 is added, and the solution is well mixed. After 40 minutes at 80° C. the solution has formed a gel. The gel is thoroughly washed with excess water for one day and stored under water to avoid drying. The water content for this gel is estimated to be 95% (by volume).

EXAMPLE 67

Polymer gel containing sulfadiazine, prepared by suspending the drug in an aqueous solution of poly(vinyl alcohol) subsequently crosslinked with methylene di(3,3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 19.6 mg (0.07 mmol) of methylene di(3,3-dimethoxypropionate) prepared as described in Example 19 in 1 ml of water and 0.20 g (0.8 mmol) of sulfadiazine, and the dispersion is well mixed. After 40 minutes at 80° C. the solution has formed a gel with the powder suspended in it. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 0.1 g (0.35 mmol) of methylene di(3,3-dimethoxypropionate) prepared as described in Example 19 and 0.20 g (0.8 mmol) of sulfadiazine, and the suspension is well mixed. After 40 minutes at 80° C. the polymer has formed a gel with the powder suspended in it. The gel is thoroughly washed with excess water for one day and stored under water to avoid drying. The water content for this gel is estimated to be 95% (by volume).

EXAMPLE 68

Polymer gel containing progesterone, prepared by suspending the drug in an aqueous solution of poly(vinyl alcohol) subsequently crosslinked with methylene di(3.3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 19.6 mg (0.07 mmol) of methylene di(3,3-dimethoxypropionate) prepared as described in Example 19 in 1 ml of water and 0.07 g (0.2 mmol) of progesterone, and the dispersion is well mixed. After 40 minutes at 80° C. the polymer has formed a gel with the powder suspended in it. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 0.1 g (0.35 mmol) of methylene di(3,3-dimethoxypropionate) prepared as described in Example 19 and 0.07 g (0.2 mmol) of progesterone, and the suspension is well mixed. After 40 minutes at 80° C. the polymer has formed a gel with the powder suspended in it. The gel is thoroughly washed with excess water for one day and stored under water to avoid drying. The water content for this gel is estimated to be 95% (by volume).

EXAMPLE 69

Polymer gel containing 5-fluorouracil, prepared by dissolving the drug in an aqueous solution of poly(vinyl alcohol) subsequently crosslinked with methylene di(3.3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 19.6 mg (0.07 mmol) of methylene di(3,3-dimethoxypropionate) prepared as described in Example 19 in 1 ml of water and 13 mg (0.1 mmol) of 5-fluorouracil dissolved in 0.5 ml water, and the solution is well mixed. After 40 minutes at 80° C. the solution has formed a gel. The gel is thoroughly washed with excess water for one day and stored under water to avoid drying. The water content for this gel is estimated to be 98% (by volume)

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 0.1 g (0.35 mmol) of methylene di(3,3-dimethoxypropionate) prepared as described in Example 19 and 13 mg (0.1 mmol) of 5-fluorouracil dissolved in 0.5 ml water, and the solution is well mixed. After 40 minutes at 80° C. the solution has formed a gel. The gel is thoroughly washed with excess water for one day and stored under water to avoid drying. The water content for this gel is estimated to be 95% (by volume).

EXAMPLE 70

Polymer gel containing Omnipaque™, prepared by dissolving the diagnostic aid in an aqueous solution of poly(vinyl alcohol) subsequently crosslinked with methylene di(3,3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 19.6 mg (0.07 mmol) of methylene di(3,3-dimethoxypropionate) prepared as described in Example 19 in 1 ml of water and 1 ml of Omnipaque™ (300 mgI/ml), and the solution is well mixed. After 40 minutes at 80° C. the solution has formed a gel. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 0.1 g (0.35 mmol) of methylene di(3,3-dimethoxypropionate) prepared as described in Example 19 and 1 ml of Omnipaque™ (300 mgI/ml), and the solution is well mixed. After 40 minutes at 80° C. the solution has formed a gel. The gel is thoroughly washed with excess water for one day and stored under water to avoid drying. The water content for this gel is estimated to be 95% (by volume).

EXAMPLE 71

Polymer gel containing magnetic starch microspheres, prepared by suspending the material in an aqueous solution of poly(vinyl alcohol) subsequently crosslinked with methylene di(3,3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 19.6 mg (0.07 mmol) of methylene di(3,3-dimethoxypropionate) prepared as described in Example 19 in 1 ml of water and 0.5 ml of a suspension containing magnetic starch microspheres prepared as described in WO 85/02772 (Schröder) (7.5 mg Fe/ml, 0.9% NaCl, 0.5% glycerol), and the suspension is well mixed. After 40 minutes at 80° C. the polymer has formed a gel with the magnetic material suspended in it. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 0.1 g (0.35 mmol) of methylene di(3,3-dimethoxypropionate) prepared as described in Example 19 and 0.5 ml of a suspension containing magnetic starch microspheres prepared as described in WO 85/02772 (Schröder) (7.5 mg Fe/ml, 0.9% NaCl, 0.5% glycerol), and the suspension is well mixed. After 40 minutes at 80° C. the polymer has formed a gel with the magnetic material suspended in it. The gel is thoroughly washed with excess water for one day and stored under water to avoid drying. The water content for this gel is estimated to be 97% (by volume).

EXAMPLE 72

Aqueous polymer gel prepared by crosslinking an aqueous solution of poly(vinyl alcohol) with methylene di(3-methoxypropenoate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution is added 55 mg (0.23 mmol) of methylene di(3-methoxypropenoate) prepared as described in Example 20 in 1 ml of 50:50 dioxane/water, and the solution is well mixed. After 40 minutes at 80° C. the solution has formed a gel. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18%) solution. To this solution is added 110 mg (0.56 mmol) of methylene di(3-methoxypropenoate) prepared as described in Example 20 in 2 ml of 50:50 dioxane/water, and the solution is well mixed. After 40 minutes at 80° C. the solution has formed a gel. The gel is thoroughly washed with excess water for one day and stored under water to avoid drying. The water content for this gel is estimated to be 97% (by volume).

EXAMPLE 73

Epoxy resin based on methylene bis(10,11-epoxyundecanoate) and an aliphatic polyamine A sample of methylene bis(10,11-epoxyundecanoate) prepared as described in Example 22 is blended with an equal weight of a commercial aliphatic polyamine curing agent. This mixture is cured on the surface of a glass plate at 70° C. The resin is observed to have hardened and good bonding is obtained within 2 hours of mixing.

EXAMPLE 74

Polymer from starch crosslinked with methylene bis(10,11-epoxyundecanoate)

Titanum (IV) isopropoxide (1.11 g, 3.9 mmol) is added to a solution of methylene bis(10,11-epoxyundecanoate) prepared as described in Example 22 (1.0 g, 2.6 mmol) and starch (1.0 g) in dry DMSO (50 ml). The reaction mixture is stirred for 4 hours at ambient temperature. Chloroform/ether (250 ml, 1:1) is added, the oily material is dissolved in water and extracted with chloroform (2× 50 ml). The aqueous phase is subjected to dialysis or gel filtration to furnish the polymer.

EXAMPLE 75

Polymer from dextran 70000 crosslinked with methylene bis (10,11-epoxyundecanoate)

Titanum (IV) isoproxide (1.11 g, 3.9 mmol) is added to a solution of methylene bis (10,11-epoxyundecanoate) prepared as described in Example 22 (1.0 g, 2.6 mmol) and dextran 70,000 in dry DMSO (50 ml). The reaction mixture is stirred for 4 hours at ambient temperature. Chloroform/ether (250 ml, 1:1) is added, the oily material is dissolved in water and extracted with chloroform (2×50 ml). The aqueous phase is subjected to dialysis or gel filtration to furnish the polymer.

EXAMPLE 76

Polymer from protein crosslinked with methylene bis(10,11-epoxyundecanoate)

Methylene bis(10,11-epoxyundecanoate) prepared as described in Example 22 (1.0 g, 2.6 mmol) is added to a solution of human serum albumin (1.0 g) in buffer (50 ml). The reaction mixture is stirred at ambient temperature overnight and evaporated. The polymer is washed several times with tetrahydrofuran and dried under reduced pressure.

The following Example from the specification of the above referenced British Patent Application No. 9114570.6 illustrates the use of cross-linking agents according to the invention in the preparation of cross-linked carbohydrate microparticles useful as an ultrasound contrast agent.

Example 77

Galactose Crosslinked with Methylene Diacrylate

A) Milled galactose 20 g of commercially available D (+) -galactose (Reinst ph.Ned.Merck) was ball-milled in an aluminium ball-mill with 3×1.5 cm diameter aluminium balls for two hours. The resulting powder mixture consisted of crystals and aggregates of galactose in the particle size range of 1–100 $\mu$m (measured light scattering, Malvern Mastersizer).

B) Milled galactose crosslinked with methylene diacrylate

A sealable 25 ml flask was loaded with 1.00 g of the product of (A) under nitrogen and to the flask was added 500 mg of methylene diacrylate prepared as in Example 2, dissolved in 10 ml dry methylene chloride under nitrogen. The sealed flask was shaken gently for 18 hours at ambient temperature. The solid content was isolated by filtration and washed several times with methylene chloride, and dried over calcium chloride in a dessicator at 5 mbar and ambient temperature for 24 hours. The resulting product was a white solid with the same appearance at the starting material. Weight: about 0.96 g.

C) Echocenicity in vitro 10 ml of propylene glycol mixed with 90 ml of 5% dextrose in water was used as a carrier liquid for determining the echogenicity of Product (B), 300 mg of the product was dispersed in 600 $\mu$l of the carrier liquid and shaken for 15 seconds. The resulting mixture was added to 6.4 ml water in the measurement cell and the acoustic effect of the substance was investigated by measuring the ultrasonic transmission through the sample using a 3.5 MHz transducer and a pulse-reflection technique. Ultrasound transmission through the sample was measured as a function of time. Results were normalized to measurements of a reference consisting of 600 $\mu$l carrier liquid in 6.4 ml water.

The results showed that Product (B) has a significant effect on ultrasonic attenuation in vitro, and that this increased attenuation persisted for several minutes.

The following Example from the specification of the above referenced British Patent Application No. 9106686.0 illustrates the preparation and use of a cross-linking agent according to the invention in the preparation of cross-linked gas filled microspheres useful as an ultrasound contrast agent.

EXAMPLE 78

A) Bis-(formyl-methyl-carbonyloxy)-methane

The preparation of the starting material, the dioxalan-protected aldehyde α-formyl-methylacetate is described by T. Hosokawa et al J. Org. Chem. Soc. 52, (1987) 1758–1764. The protected aldehyde (6.0 g, 3.75 mmol) is treated with a mixture of 2N aqueous potassium hydroxide and tetrahydrofuran 20:80 (v/v) at reflux for 8 hours. The pH is adjusted to 8 using diluted HCl, and the mixture is evaporated to dryness. The solid is mixed with 100 ml freshly distilled and dried DMF, and after 30 mins at 60° C. the undissolved material is filtered off. Diiodomethane (150 $\mu$l, 1.87 mmol) is added dropwise during 5 mins to the solution at 60° C. as described in WO 89/00988 page 13 (Nycomed AS). The precipitate is removed by filtration after stirring for 4 days, and the solvent removed at reduced pressure. The dioxalane protection is removed as decsribed by A. Grieco et al J. Am. Chem. Soc. 99, (1977) 5773–5780: the residue is dissolved in 60 ml tetra-hydrofuran, added 20 ml 5% aqueous HCl and stirred for 20 hours at ambient temperature. The reaction mixture is evaporated to dryness under reduced pressure to yield the product.

B) Preparation of cross-linked gas filled albumin microspheres:

1. Gas-filled albumin microspheres are prepared according to EP-A-0359 246 and resuspended to homogeneity by gentle rolling on a vial roller.
2. 25 ml of the suspension are poured into a 25 ml separating funnel and left for 30 min. The bottom 20 ml are discarded.
3. To the remaining 5 ml is added 20 ml of a phosphate buffer (20 mM NaPO$_4$, pH 7.0), and the resulting suspension is transferred to a vial with a cap septum.
4. The vial is centrifuged upside down at 170×g for 5 min.
5. The solution underneath the microsphere layer is withdrawn using a syringe, and the microspheres are resuspended in 25 ml of the phosphate buffer by 10 min of gentle rolling.
6. Points 4 and 5 are repeated twice.
7. The resulting suspension is centrifuged as in point 4, and the microspheres are resuspended in the phosphate buffer to a final concentration of about 5×10$^8$ particles per ml.

8. The crosslinker methylene bis(α-formylacetate), prepared as described in Preparation 1, is added to the suspension, and the crosslinking reaction is allowed to proceed for the desired time (usually 30–60 min) under gentle rolling.
9. 1.5M Tris-HCl-buffer (pH 8.8) is added to a final concentration of 0.25M, and the suspension is rolled gently for 10 min.
10. The vial is centrifuged as in point 4, and the solution underneath the microsphere layer is removed as in point 5.
11. The microspheres are resuspended in phosphate buffer (same volume as final volume in point 9), and the suspension is rolled for 10 min.
12. Points 10 and 11 are repeated twice.
13. The resulting suspension is centrifuged as in point 4, and the microspheres are resuspended in the phosphate buffer to a final concentration of about $5 \times 10^8$ particles per ml.
14. This final suspension of crosslinked gas/albumin microspheres is stored at 4° C.

We claim:

1. A method of crosslinking a crosslinkable protein or carbohydrate substrate to form a crosslinked substrate in which the crosslinking groups are biodegradable, said method comprising reacting said crosslinkable substrate with a crosslinking agent of formula (IIIa)

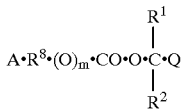

(IIIa)

wherein Q is selected from the group consisting of halogen atoms, alkanesulphonyloxy groups, arenesulphonyloxy groups and groups of formula —O.CO.(O)$_n$.R$^9$.B;

m and n may be the same or different and are each selected from the group consisting of zero and 1;

R$^1$ and R$^2$ may be the same or different and are each selected from the group consisting of hydrogen atoms, aliphatic, cycloalkyl, araliphatic, aryl and heterocyclic groups, groups of formula —O.CO.(O)$_m$.R$^8$.A and groups of formula —O.CO.(O)$_n$.R$^9$.B, or R$^1$ and R$^2$ together form an alkylene, alkenylene, alkylidene or alkenylidene group;

R$^8$ and any group R$^9$ may be the same or different and are each selected from the group consisting of alkylene groups; alkenylene groups; phenyleneethynylmethylene; cycloalkylene groups; arylene groups; $C_{1-6}$ alkyl substituted arylene groups; aralkylene groups; $C_{1-6}$ alkyl substituted aralkylene groups; heterocyclic groups; any of the foregoing substituted by one or more of oxo, thio, hydroxyl, etherified hydroxyl, esterified hydroxyl, etherified thiol, N—($C_{1-6}$ alkyl) amino, N—($C_{1-6}$ acyl) amino, N—($C_{1-6}$ acyl) —N—($C_{1-6}$ alkyl) amino, carbamoyl, N—($C_{1-6}$ alkyl) carbamoyl and halogen; and any of the foregoing interrupted by oxygen atoms;

and A and any group B may be the same or different and each represents a reactive functional grouping selected from the group consisting of a halogen atom, an aryl halide group, an alkanesulphonyloxy group, an arenesulphonyloxy group, an α-halomethyl carbonyl group, a carboxyl group, an anhydride group, an optionally sulphonated succinimidyloxy group, a hydroxyl group, a mercapto group, an alkene group, an α, β-alkene ester group, an α, β-alkene amide group, an α, β-alkene ketone group, a conjugated diyne group, a conjugated enyne group, an epoxy group, an amino group, a diazo group, an imidoester group, an alkyl halide group, an aralkyl halide group, a nitroaryl halide group, an aryl azide group, a diazo group, a diazirine group, a formyl group or the dimethyl acetal thereof, an acetyl group, an isocyanate group, an isothiocyanate group, a semicarbazide group, a thiosemicarbazide group, a carboxy (nitro) phenol group, an alkanoyl azide group, a hydrazine group, a haloformate group, an optionally sulphonated maleimide group, a nitrosourea group, an s-triazine group, an aziridine group and a pyridyl disulphide group;

or at least one of A.R$^8$— and any group —R$^9$.B represents an optionally substituted vinyl group.

2. The method of claim 1 wherein the crosslinking agent is a compound of formula (IIIa) in which R$^1$ and R$^2$ are each selected from the group consisting of hydrogen atoms and $C_{1-4}$ alkyl groups.

3. The method of claim 1 wherein the crosslinking agent is a compound of formula (IIIa) in which R$^8$ and any group R$^9$ are selected from the group consisting of $C_{1-30}$ alkylene; $C_{1-30}$ alkylene interrupted by one or more oxy, carbonyloxy or oxycarbonyl groups; phenylene; phenyleneoxymethylene and phenyleneethynylmethylene.

4. The method of claim 1 wherein the crosslinking agent is methylene bis(16-hydroxyhexadecanoate).

5. The method of claim 1 wherein the crosslinkable substrate is an ultrasound contrast agent.

6. The method of claim 1 wherein the cross-linking agent is methylene diacrylate.

7. The method of claim 1 wherein the cross-linkable substrate is galactose.

* * * * *